US010074173B2

(12) United States Patent
Miller et al.

(10) Patent No.: US 10,074,173 B2
(45) Date of Patent: Sep. 11, 2018

(54) METHODS AND SYSTEMS FOR ANALYZING ANATOMY FROM MULTIPLE GRANULARITY LEVELS

(71) Applicant: The Johns Hopkins University, Baltimore, MD (US)

(72) Inventors: Michael I. Miller, Pikesville, MD (US); Susumu Mori, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/101,820

(22) PCT Filed: Dec. 8, 2014

(86) PCT No.: PCT/US2014/069161
§ 371 (c)(1),
(2) Date: Jun. 3, 2016

(87) PCT Pub. No.: WO2015/085320
PCT Pub. Date: Jun. 11, 2015

(65) Prior Publication Data

US 2016/0307316 A1 Oct. 20, 2016

Related U.S. Application Data

(60) Provisional application No. 61/913,098, filed on Dec. 6, 2013.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0037* (2013.01); *A61B 5/0042* (2013.01);
(Continued)

(58) Field of Classification Search
CPC . G06T 7/0012; G06T 7/11; G06T 7/40; G06T 2207/10081; G06T 2207/10088;
(Continued)

(56) References Cited

U.S. PATENT DOCUMENTS 6,611,630 B1 8/2003 Miller et al.
7,142,633 B2 * 11/2006 Eberhard .............. A61B 6/482 378/62
(Continued)

FOREIGN PATENT DOCUMENTS

WO WO-2010005973 A2 1/2010

OTHER PUBLICATIONS

Aljabar et al., "Multi-atlas based segmentation of brain images: Atlas selection and its effect on accuracy," NeuroImage, 46(3):726-38 (2009).
(Continued)

*Primary Examiner* — Ali Bayat
(74) *Attorney, Agent, or Firm* — Venable, LLP; Henry J. Daley; Fusheng Xu

(57) ABSTRACT

A method, computer system and computer readable storage medium for searching for one or more images having a region of interest similar to the region of a subject, including: receiving imaging data comprising a plurality of image elements of the region of interest of the subject; segmenting the imaging data of the region of interest of the subject into a plurality of sub-regions corresponding to various structures at a plurality of levels of granularity, the plurality of levels of granularity having a relationship such that a level of granularity has fewer structures at a lower level of granularity; and calculating at each of the plurality of levels of granularity an abnormality factor or risk factor for the segmented various structures of said region of interest, to provide a segmented said region of interest of said subject
(Continued)

with at least one of said abnormality factor or risk factor associated therewith.

60 Claims, 14 Drawing Sheets

(51) Int. Cl.
*A61B 5/055* (2006.01)
*A61B 5/00* (2006.01)
*A61B 6/03* (2006.01)
*A61B 8/08* (2006.01)
*G06T 7/11* (2017.01)

(52) U.S. Cl.
CPC ............ *A61B 5/055* (2013.01); *A61B 5/4064* (2013.01); *A61B 6/032* (2013.01); *A61B 6/037* (2013.01); *A61B 8/08* (2013.01); *G06T 7/11* (2017.01); *A61B 2576/026* (2013.01); *G06T 2207/10081* (2013.01); *G06T 2207/10088* (2013.01); *G06T 2207/10104* (2013.01); *G06T 2207/10132* (2013.01); *G06T 2207/10136* (2013.01); *G06T 2207/20128* (2013.01); *G06T 2207/30008* (2013.01); *G06T 2207/30016* (2013.01); *G06T 2207/30048* (2013.01); *G06T 2207/30056* (2013.01); *G06T 2207/30061* (2013.01); *G06T 2207/30088* (2013.01)

(58) Field of Classification Search
CPC . G06T 2207/10104; G06T 2207/10132; G06T 2207/10136; G06T 2207/20101; G06T 2207/30004; A61B 5/0037; A61B 5/0042; A61B 5/055; A61B 5/4064; A61B 6/037; A61B 8/08
See application file for complete search history.

(56) References Cited

U.S. PATENT DOCUMENTS

| | | | | |
|---|---|---|---|---|
| 7,324,842 | B2 | 1/2008 | Dale et al. | |
| 7,545,997 | B2 * | 6/2009 | Lieberman | H04N 1/40068 382/101 |
| 7,783,132 | B2 | 8/2010 | Nowinski et al. | |
| 8,456,163 | B2 * | 6/2013 | Zhao | G01R 33/4826 324/307 |
| 2012/0155733 | A1 | 6/2012 | Wagenkenecht | |
| 2013/0102877 | A1 | 4/2013 | Mori et al. | |
| 2013/0279722 | A1 | 10/2013 | Lautzenhiser et al. | |
| 2016/0225146 | A1 * | 8/2016 | Frank | A61B 5/055 |
| 2017/0193161 | A1 * | 7/2017 | Sapiro | G06F 19/321 |

OTHER PUBLICATIONS

Artaechevarria et al., "Combination Strategies in Multi-Atlas Image Segmentation: Application to Brain MR Data," IEEE Trans. Med. Imaging, 28(8):1266-77 (2009).
Ashburner et al., "Voxel-Based Morphometry—The Methods," NeuroImage, 11:805-821 (2000).
Ceritoglu et al., "Multi-contrast large deformation diffeomorphic metric mapping for diffusion tensor imaging," NeuroImage, 47(2):618-627 (2009).
Christensen et al., "Volumetric Transformation of Brain Anatomy," IEEE Trans. Med. Imaging, 16(6):864-877 (1997).
Davatzikos, "Why voxel-based morphometric analysis should be used with great caution when characterizing group differences," NeuroImage, 23(1):17-20 (2004).
Djamanakova et al., "Diffeomorphic brain mapping based on T1-weighted images: Improvement of registration accuracy by multichannel mapping," Journal of Magnetic Resonance Imaging, 37(1):76-84 (2013).
Faria et al., "Atlas-based analysis of neurodevelopment from infancy to adulthood using diffusion tensor imaging and applications for automated abnormality detection," NeuroImage, 52(2):415-428 (2010).
Heckemann et al., "Automatic anatomical brain MRI segmentation combining label propagation and decision fusion," NeuroImage, 33(1):115-26 (2006).
Jack et al., "The Alzheimer's Disease Neuroimaging Initiative (ADNI): MRI methods," J. Magn. Reson. Imaging, 27(4):685-691 (2008).
Landman et al., " Multi-parametric neuroimaging reproducibility: a 3-T resource study," NeuroImage, 54(4):2854-2866 (2011).
Langerak et al., "Label Fusion in Atlas-Based Segmentation Using a Selective and Iterative Method for Performance Level Estimation (SIMPLE)," IEEE Trans. Med. Imaging, 29(12):2000-2008 (2010).
Li et al., mristudio.org, Johns Hopkins University (last accessed May 26, 2017).
Lotjonen et al., "Fast and robust multi-atlas segmentation of brain magnetic resonance images," NeuroImage 49(3):2352-2365 (2010).
McKhann et al., "Clinical diagnosis of Alzheimer's disease: Report of the NINCDS-ADRDA Work Group under the auspices of Department of Health and Human Services Task Force on Alzheimer's Disease," Neurology, 34(7):939-44 (1984).
Mielke et al., "Regionally-Specific Diffusion Tensor Imaging in Mild Cognitive Impairment and Alzheimer's Disease," NeuroImage, 46(1):47-55 (2009).
Mori et al., "Stereotaxic white matter atlas based on diffusion tensor imaging in an ICBM template," NeuroImage, 40(2):570-582 (2008).
Mori et al., Atlas-Based Neuroinformatics via MRI: Harnessing Information from Past Clinical Cases and Quantitative Image Analysis for Patient Care, Annu. Rev. Biomed. Eng. 15:71-92 (2013).
Munoz-Moreno et al., "A Magnetic Resonance Image Based Atlas of the Rabbit Brain for Automatic Parcellation," PLOS One, 8(7): e67418 (2013).
Oishi et al., "Atlas-based whole brain white matter analysis using Large Deformation Diffeomorphic Metric Mapping: Application to normal elderly and Alzheimer's disease participants," NeuroImage, 46:486-499 (2009).
Puelles et al., "A developmental ontology for the mammalian brain based on the prosomeric model," Trends in Neurosciences, 36(10):570-578 (2010).
Alzheimer's Association, "Research consent for cognitively impaired adults: recommendations for institutional review boards and investigators," Alzheimer Dis. Assoc. Disord., 18(3):171-175 (2004).
Rohlfing et al., "Evaluation of atlas selection strategies for atlas-based image segmentation with application to confocal microscopy images of bee brains," NeuroImage, 21(4):1428-1442 (2004).
Tang et al., "Bayesian Parameter Estimation and Segmentation in the Multi-Atlas Random Orbit Model," PLOS One, 8(6): e65591 (2013).
Vogt, "Spatio-structural granularity of biological material entities," BMC Bioinformatics, 11:289 (2010).
Warfield et al., "Simultaneous Truth and Performance Level Estimation (STAPLE): An Algorithm for the Validation of Image Segmentation," IEEE Trans. Med. Imaging, pp. 1-24 (2004).
Zhang et al., "Evaluation of group-specific, whole-brain atlas generation using Volume-based Template Estimation (VTE): Application to normal and Alzheimer's populations," NeuroImage 84: 406-419 (2014).
Djamanikova et al., "Tools for Multiple Granularity Analysis of Brain MRI Data for Individualized Image Analysis," Neuroimage, 101:168-76 (Nov. 2014).

* cited by examiner

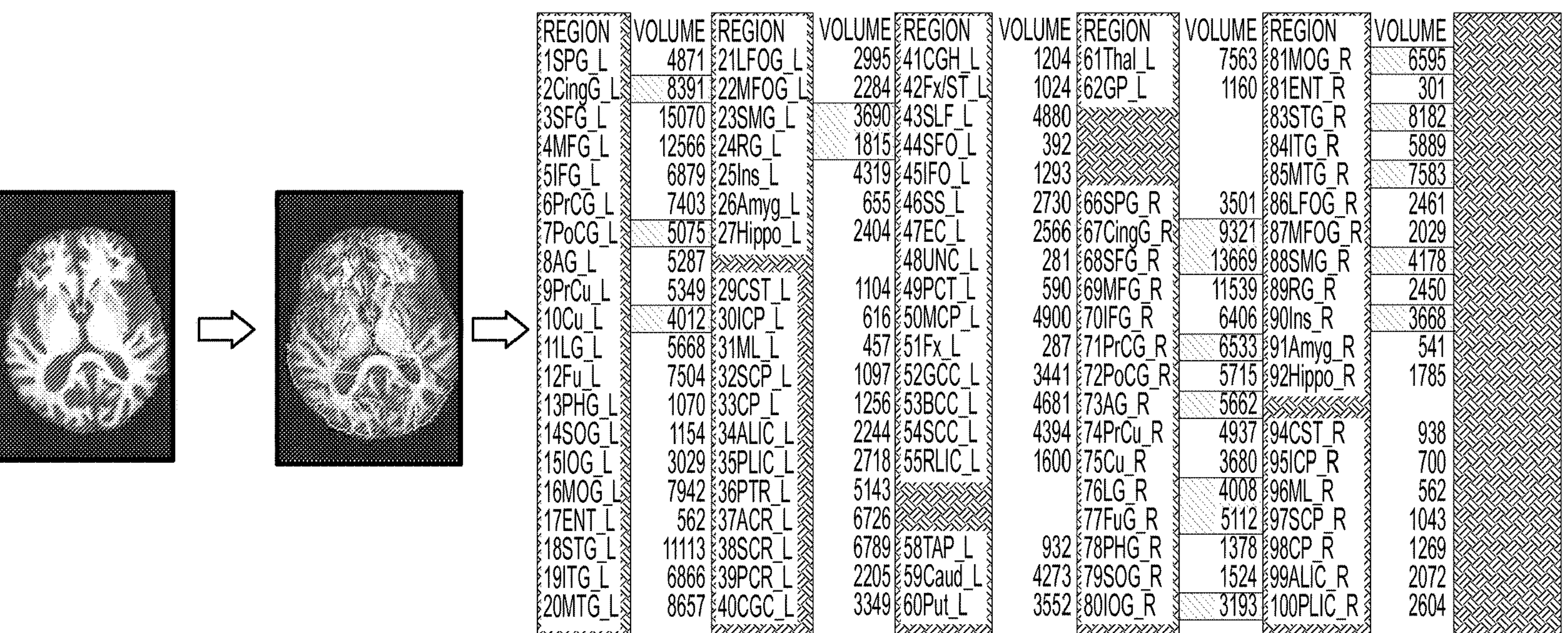

| REGION | VOLUME | REGION | VOLUME | REGION | VOLUME | REGION | VOLUME | REGION | VOLUME |
|---|---|---|---|---|---|---|---|---|---|
| 1SPG_L | 4871 | 21LFOG_L | 2995 | 41CGH_L | 1204 | 61Thal_L | 7563 | 81MOG_R | 6595 |
| 2CingG_L | 8391 | 22MFOG_L | 2284 | 42Fx/ST_L | 1024 | 62GP_L | 1160 | 81ENT_R | 301 |
| 3SFG_L | 15070 | 23SMG_L | 3690 | 43SLF_L | 4880 | | | 83STG_R | 8182 |
| 4MFG_L | 12566 | 24RG_L | 1815 | 44SFO_L | 392 | | | 84ITG_R | 5889 |
| 5IFG_L | 6879 | 25Ins_L | 4319 | 45IFO_L | 1293 | | | 85MTG_R | 7583 |
| 6PrCG_L | 7403 | 26Amyg_L | 655 | 46SS_L | 2730 | 66SPG_R | 3501 | 86LFOG_R | 2461 |
| 7PoCG_L | 5075 | 27Hippo_L | 2404 | 47EC_L | 2566 | 67CingG_R | 9321 | 87MFOG_R | 2029 |
| 8AG_L | 5287 | | | 48UNC_L | 281 | 68SFG_R | 13669 | 88SMG_R | 4178 |
| 9PrCu_L | 5349 | 29CST_L | 1104 | 49PCT_L | 590 | 69MFG_R | 11539 | 89RG_R | 2450 |
| 10Cu_L | 4012 | 30ICP_L | 616 | 50MCP_L | 4900 | 70IFG_R | 6406 | 90Ins_R | 3668 |
| 11LG_L | 5668 | 31ML_L | 457 | 51Fx_L | 287 | 71PrCG_R | 6533 | 91Amyg_R | 541 |
| 12Fu_L | 7504 | 32SCP_L | 1097 | 52GCC_L | 3441 | 72PoCG_R | 5715 | 92Hippo_R | 1785 |
| 13PHG_L | 1070 | 33CP_L | 1256 | 53BCC_L | 4681 | 73AG_R | 5662 | | |
| 14SOG_L | 1154 | 34ALIC_L | 2244 | 54SCC_L | 4394 | 74PrCu_R | 4937 | 94CST_R | 938 |
| 15IOG_L | 3029 | 35PLIC_L | 2718 | 55RLIC_L | 1600 | 75Cu_R | 3680 | 95ICP_R | 700 |
| 16MOG_L | 7942 | 36PTR_L | 5143 | | | 76LG_R | 4008 | 96ML_R | 562 |
| 17ENT_L | 562 | 37ACR_L | 6726 | | | 77FuG_R | 5112 | 97SCP_R | 1043 |
| 18STG_L | 11113 | 38SCR_L | 6789 | 58TAP_L | 932 | 78PHG_R | 1378 | 98CP_R | 1269 |
| 19ITG_L | 6866 | 39PCR_L | 2205 | 59Caud_L | 4273 | 79SOG_R | 1524 | 99ALIC_R | 2072 |
| 20MTG_L | 8657 | 40CGC_L | 3349 | 60Put_L | 3552 | 80IOG_R | 3193 | 100PLIC_R | 2604 |

Figure 2

METHODS AND SYSTEMS FOR ANALYZING ANATOMY FROM MULTIPLE GRANULARITY LEVELS

CROSS REFERENCE TO RELATED APPLICATIONS

This is a national stage application under 35 U.S.C. § 371 of PCT/US2014/069161 filed Dec. 8, 2014, which claims the benefit of U.S. Provisional Application No. 61/913,098 filed Dec. 6, 2013, which is hereby incorporated herein by reference in its entirety.

STATEMENT OF GOVERNMENT SUPPORT

This invention was made with government support under UL1RR025005, R21AG033774, NS084957, EB017638, EB015909, and NS058299 awarded by the Department of Health and Human Services NCRR/NIH and NIH Roadmap for Medical Research. The government has certain rights in this invention.

TECHNICAL FIELD

This disclosure relates generally to analyzing anatomy from multiple granularity levels and more particularly to methods, system, and media for analyzing anatomy from multiple granularity levels.

BACKGROUND

Medical imaging such as MRI and CT is playing a crucial role for daily image-based diagnosis in Radiology. The images are currently visually evaluated by trained physicians and medical decisions are being made by subjective judgments. Currently computational supports for image reading are used only for limited tissue areas and a vast majority of the images are evaluated without computational supports.

When physicians evaluate anatomy, they have an ability to dynamically control the level of anatomical granularity they are inspecting. This disclosure is based on our discovery that this dynamic granularity control is the reason why past computational support could never approach human's ability to comprehend anatomy and accurately detect abnormalities in patients.

For example, when a radiologist is reading an MR image of a dementia patient, the doctor first can evaluate the overall brain atrophy. In this case, the size of the entire hemisphere and the ventricles are evaluated. The brainstem and the cerebellum size could also be evaluated as a clue for hemispheric-specific atrophy or to rule out the involvement of the cerebellum. Then the overall status of the cortex, the white matter, and the deep gray matter structures are evaluated. The inspection continues to smaller granularity levels, in which atrophy of each lobes and specific gray matter nuclei are evaluated. For example, the involvement of only the temporal lobe could indicate a specific disease class. Intensity abnormalities in the white matter could also indicate diffuse axonal injuries. The granularity level of the visual inspection could also increase substantially when the doctor is seeking for a certain type of small anatomical signatures; such as the volume loss of the caudate in the Huntington's disease or intensity abnormality in the pons for a certain type of ataxia.

This type of dynamic granularity control has never been implemented and deployed in the computational diagnosis supports in the past. For quantitative image analysis, the highest granularity level, which is one voxel, has been historically used. This means, every voxel is measured and tested for an existence of the abnormality. As being the smallest unit of imaging, the voxel-based analysis carries the maximum amount of anatomical information and in theory it is capable of detecting any type of abnormalities; thus evaluation with lower granularity levels are not necessary. This type of analysis, however, fails to replace human judgment; a human does not evaluate images in voxel levels. Voxel-based analysis is widely used for quantitative analysis of brain MRI. While it provides the highest granularity level of spatial information (i.e. each voxel), the sheer number of the voxels and noisy information from each voxel often leads to low sensitivity for abnormality detection. Thus, the primary reason of the failure is that information from each voxel is noisy and there are too many voxels.

To ameliorate this problem, spatial filtering, which effectively makes the voxel size larger, has been used, leading to decreased granularity levels. However, as granularity is reduced, information may also be lost. As another means of ameliorating this issue, it is common to introduce granularity reduction by applying isotropic spatial filtering. However, again, this type of isotropic reduction of the image granularity level is not what human does; they control granularity based on anatomy.

What is needed are methods, systems, and media that analyze anatomy from multiple granularity levels.

SUMMARY

Various embodiments are generally directed to gross feature recognition of anatomical images to overcome the aforementioned problems.

In one aspect of the invention, a computer-implemented method of segmenting imaging data of at least one subject, includes receiving imaging data having a plurality of image elements of a region of interest of the at least one subject; segmenting, using at least one data processor, the imaging data of the region of interest of the at least one subject into a plurality of sub-regions corresponding to various structures at a plurality of levels of granularity, the plurality of levels of granularity having a relationship such that a level of granularity has fewer structures than at a lower level of granularity; and calculating at each of the plurality of levels of granularity an abnormality factor or risk factor for the segmented various structures of said region of interest, to provide a segmented said region of interest of said subject with at least one of said abnormality factor or risk factor associated therewith.

In another aspect of the invention, a computer system for segmenting imaging data of at least one subject includes a memory storing computer-executable instructions; and at least one data processor that is coupled to the memory and that is configured to execute the computer-executable instructions to perform the following steps: 1) receive imaging data having a plurality of image elements of a region of interest of the at least one subject; 2) segment the imaging data of the region of interest of the at least one subject into a plurality of sub-regions corresponding to various structures at a plurality of levels of granularity, the plurality of levels of granularity having a relationship such that a level of granularity has fewer structures at a lower level of granularity; and 3) calculate at each of the plurality of levels of granularity an abnormality factor or risk factor for the segmented various structures of said region of interest, to provide a segmented said region of interest of said subject with at least one of said abnormality factor or risk factor associated therewith.

In another aspect of the invention, a non-transitory computer readable storage medium for segmenting imaging data of at least one subject, includes instructions that, when executed by at least one data processor, enable a computing system to: 1) receive imaging data having a plurality of image elements of a region of interest of the at least one subject; 2) segment the imaging data of the region of interest of the at least one subject into a plurality of sub-regions corresponding to various structures at a plurality of levels of granularity, the plurality of levels of granularity having a relationship such that a level of granularity has fewer structures at a lower level of granularity; and calculate at each of the plurality of levels of granularity an abnormality factor or risk factor for the segmented various structures of said region of interest, to provide a segmented said region of interest of said subject with at least one of said abnormality factor or risk factor associated therewith.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

Embodiments will now be described in connection with the associated drawings, in which:

FIG. 2 depicts automated segmentation of the brain into 200 structures by applying the template atlas information.

DETAILED DESCRIPTION OF THE DRAWINGS

Figure 1:
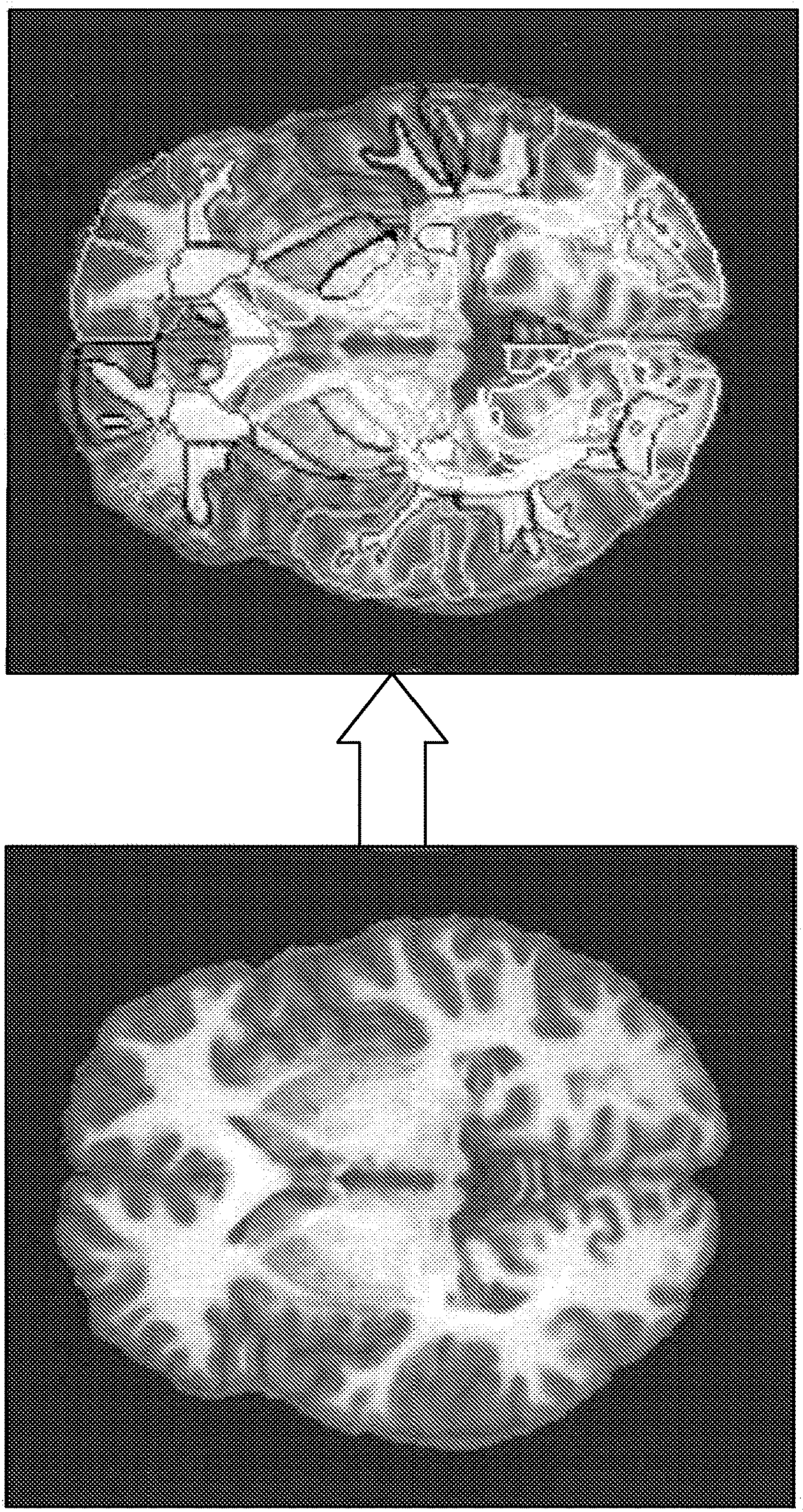
FIG. 1 depicts a template atlas that defines 200 structures.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference herein in their entireties as if each had been individually incorporated.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® NT/98/2000/XP/Vista/Windows 7/8/etc. available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium (e.g., a non-transitory computer readable storage medium) that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but is not limited to) a hard disk drive and/or a removable storage drive, representing a floppy diskette drive, a magnetic tape drive, an optical disk drive, a compact disk drive CD-ROM, flash memory, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In alternative illustrative embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

The computer may also include an input device may include any mechanism or combination of mechanisms that may permit information to be input into the computer system from, e.g., a user. The input device may include logic configured to receive information for the computer system from, e.g. a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or other camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, that are connected to a communication infrastructure (e.g., but not limited to, a communications bus, cross-over bar, interconnect, or network, etc.). The term data processor may include any type of processor, microprocessor and/or processing logic that may interpret and execute instructions (e.g., for example, a field programmable gate array (FPGA)). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CATS, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

An embodiment of the invention tells that the image granularity level has to be controlled based on anatomy and this describes how it can be achieved.

In this disclosure, a structure definition file is used. This typically is a structure-template atlas which contains pre-defined structures. For anatomical reference and quantitative analysis of medical imaging data, atlases play crucial roles. Inside the atlases, locations and boundaries of various structures are defined. This knowledge is then applied to the medical image of interest. For example, given an atlas of the human body, in which 1,000 structures are defined, by applying this knowledge to a whole-body CT image, these 1,000 structures can be defined manually or with computational aid such as warping the atlas to the image. Once the 1,000 structures are defined, then their volumes can be measured to characterize the anatomical features of the patient. In some embodiments of the invention, the term "granularity" is used to describe the level of fineness of defined structures in the atlas. If 10,000 structures are defined, instead of 1,000, the anatomy of the body can be characterized in more detail. Atlases are usually created as a generic purpose and there is often no a priori assumption about how it will be used for which pathological states. As such, it is difficult to pre-determine the most appropriate granularity level of the atlas. In the medical image, the finest granularity is determined by the imaging voxel. The lowest granularity level is the entire object of interest. There are almost infinite numbers of granularity levels to choose and super-structures to create. The proper creation of the hierarchical tables to control the granularity levels and the generation of various super-structures that consists of multiple voxels would be a very powerful method to fully exploit the anatomical information encoded in medical images. Thus, depending on the medical or biological questions, a cellular analysis may not always be better than an organ-level analysis to answer a medical question.

FIG. 1 depicts a template atlas that defines 200 structures. For example, this figure shows in a first step of one embodiment that a brain image is parcellated into approximately 200 defined structures.

In the second step of one embodiment, this structural template is applied to another image of a patient of interest, automatically defining the 200 structures in the patient. This can be also achieved by preparing multiple template atlases, which are all applied to the patient image and by performing a population-based labeling of the 200 structures.

In the third step of one embodiment, the first and second steps can be repeated to various normal and abnormal brains. From the abnormal brains, we can calculate aggregated reports such as the average volume and image intensity of each defined structure. Based on these normal values, we can judge if the values from a patient is statistically abnormal or not. For example, if we are measuring volumes of the 200 defined structures, we can obtain 200 statistical results, detecting abnormally large or small structures out of the 200 defined structures.

FIG. 2 depicts automated segmentation of the brain into 200 structures by applying the template atlas information. This converts the image information into a 200-element vector, representing the volumes of all defined structures.

For example, in this example, a patient brain is parcellated to the 200 structures and the volume of each structure can be measured. The values can then be compared to normal values and the abnormally small structures can be highlighted (values three standard deviations off normal values are indicated by light blue and four standard deviations off are by dark blue).

Figure 3:
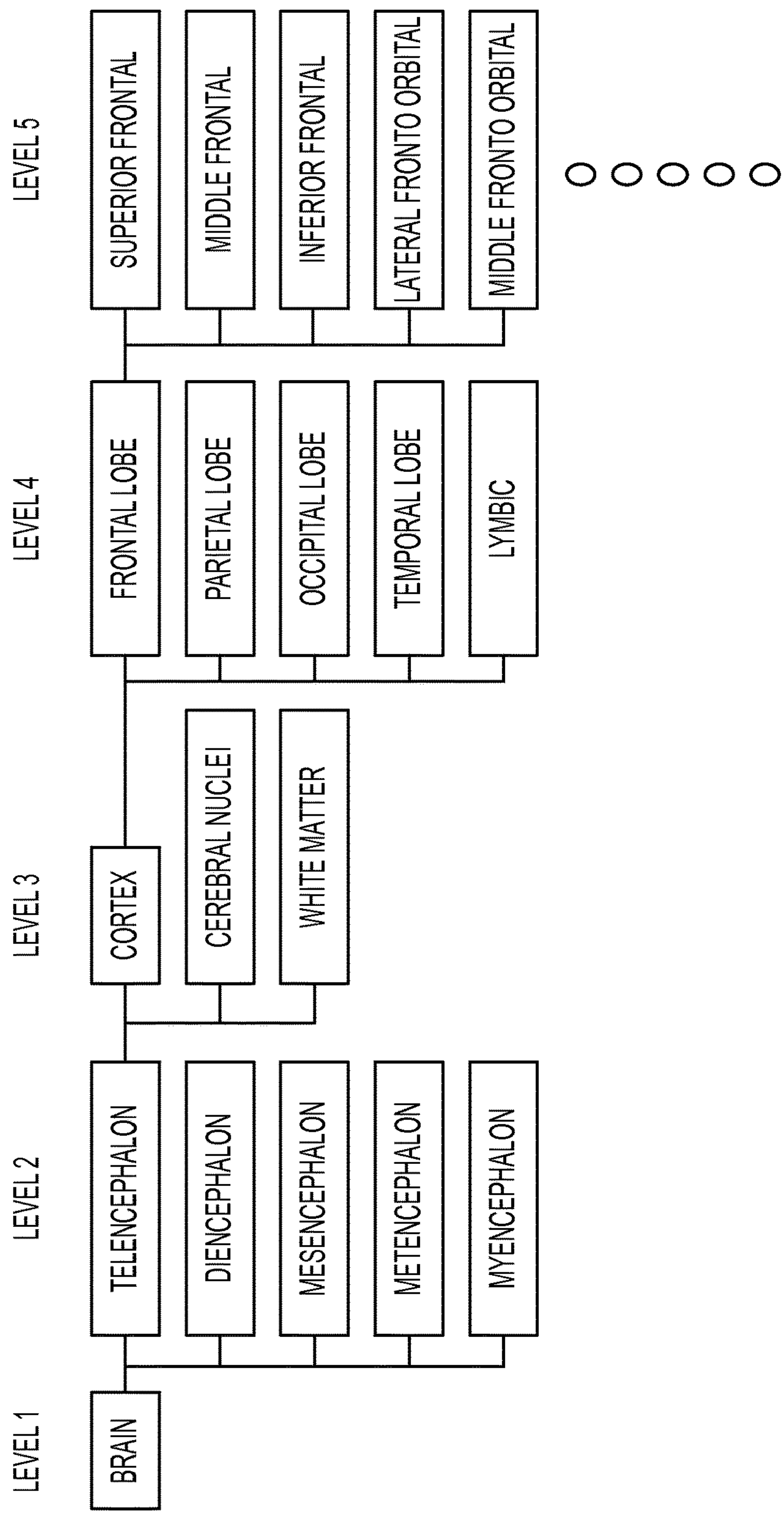
FIG. 3 depicts a hierarchical definition of the brain structures with different levels of granularity.

In the fourth step of one embodiment, the granularity levels can be dynamically controlled by using a hierarchical relationship table. One of the most natural ways to create a hierarchical relationship is based on the structural criteria following the development. For example, the brain can be divided into different numbers of structures as shown below FIG. 3 depicts a hierarchical definition of the brain structures with different levels of granularity.

In the lowest granularity (Level 1), the brain is defined as one entity and the volume measurement yields the whole brain volume. In the next level of the granularity, the brain is separated into five different regions; the total brain volume is divided into five volumes, which gives the information about the basic proportion of the brain. For example, ataxia patients would have disproportionally small metencephalon (cerebellum). Likewise, the brain can be divided into smaller and smaller units as we go down the levels of the hierarchical tree. In this example, the lowest level (Level 5) contains the information about the volumes of the 200 structures defined in FIGS. 1 and 2.

An important aspect is that while the information from the lowest level (highest granularity) has the more amount of information (for example, the largest number of defined structures, say, 200), the information at the higher level may not be obtained from the lower level information.

If we keep increasing the granularity, the highest granularity we can achieve is one voxel. For example, if we have 1×1×1 mm voxel resolution, one brain with 1.2 L of volume would have 1.2 million voxels. Each voxel could serve as one structural unit. One assumption we can make is, if we examine every single voxel, the entire brain can be examined, and therefore lower granularity analyses, in which multiple voxels are inevitably combined, is not necessary. This assumption is not always true because in reality, identification of corresponding voxels across subject contains inaccuracy and information from each voxel is noisy. This leads to the necessity to group and average voxel properties, which would increase the signal-to-noise. This operation is typically done by applying isotropic spatial filtering, meaning voxels within a predefined radius are averaged, effectively reducing the image spatial resolution.

This disclosure makes clear that, when we group voxels, we should provide anatomical knowledge and voxels should be grouped based on anatomy. Our Level 5 atlas provides anatomical knowledge to define structures. As we decrease the granularity (going up the Levels), multiple structures are combined, which provides different views to examine the brain anatomy. For example, the "frontal lobe" defined in Level 4 may provide 5% loss of volumes. This may not be detectable by measuring the volumes of the five constituents of the frontal lobe in Level 5 because 5% loss is too small to detect in Level 5 due to an expected increase in the noise in the lower levels. Conversely, the Level 5 analysis can find that the 5% loss of the frontal lobe is due to 20% volume loss of only one of the five constituents, say, superior frontal gyms, which can provide a more specific view than saying 5% volume loss of the frontal lobe. In this manner, analysis at different granularity levels can provide different anatomical views about the anatomical status, compared to the single-level analysis.

Thus, FIGS. 2 and 3 show a computer-implemented method, computer system or computer readable medium for segmenting a region of interest 102 of a subject. The method can include receiving imaging data that can include a plurality of image elements of the region of interest 102 of the subject. The method can also include segmenting, using at least one data processor, the imaging data of the region of interest of the subject into a plurality of sub-regions corresponding to various structures 104 at a plurality of levels of granularity, the plurality of levels of granularity can have a hierarchical relationship such that a level of granularity has fewer structures than a lower level of granularity. The method can further include calculating at each of the plurality of levels of granularity an abnormality factor or risk factor for the segmented structures of the region of interest 102. In one embodiment, the structural units can be obtained in a variety of ways, each of the units being defined in a particular way. Higher-order structures can be defined by combining the parts, and multiple ways of defining the hierarchy are possible.

In another embodiment, the method can further include providing at least one template atlas for the region of interest of the subject. In this embodiment, the various structures at each level of granularity can be predefined in the at least one template atlas, and the segmenting can include applying the at least one template atlas to the received imaging data at each level of granularity. In one embodiment, the received imaging data can be co-registered to the at least one template atlas. In this embodiment, the structural units can be predefined in the atlases, which are transferred to the imaging data. The scheme of the hierarchical relationship in one embodiment should be compatible with the pre-defined structures in the atlases; if the hierarchical relationship is based on structural units A, B, C, D, these structures need to be defined in the atlases.

In some embodiments, the plurality of sub-regions corresponding to the various structures are non-randomly selected, and they can be grouped by a same matter or tissue (e.g., gray matter, white matter). For example, anatomical features can be used as a reason to combine the various structures into groups. Thus, the groupings can obey a biological system (e.g., central nervous system).

In one embodiment, the at least one template atlas can include at least one of normal region of interest template data and abnormal region of interest template data. In one embodiment, for each atlas in the at least one template atlas, the method can include filtering the image to a granularity of the atlas before co-registering the image to the atlas.

Further, the segmenting can include applying the received imaging data to the normal region of interest template data and/or abnormal region of interest template data. Further, the calculating can be based on the received imaging data fitting within either the normal region of interest template data or the abnormal region of interest template data at a statistically significant level.

Additionally, the segmenting can include measuring at least one of sizes, shapes and intensities of the various structures at each level of granularity, and performing population-based labeling of the various structures to characterize anatomical features of the region of interest. For example, an anatomical feature can be a characteristic in a leg such as a tissue size. Suppose a researcher is interested in anatomical features that can predict the risk of a walking disability due to broken bones in aged populations. After finding 200 clinical data points in which 40 patients suffered from the walking disability, the researcher can measure the volumes of all 1,000 defined structures of the 40 patients and compare them to the 160 subjects without walking disability. He can find that the volumes of the several bones in the legs and the feet were significantly lower.

In this hypothetical scenario, there is no guarantee that the atlas employed in the study defines the structure in the way most appropriate for the study. First of all, there are almost infinite ways to define structures in an atlas. The entire right leg bones can be defined as a "leg bone" or the four major bones in the leg can be defined separately. Then one part of the leg bone, say the tibia, can be divided further into smaller units such as the lateral tibia condyle, the medial tibia condyle, etc. Such sub-divisions can be extended further into microscopic levels such as intra-bone structures and constituent cells. The more structures are defined in the atlas, the more anatomical information is added. Going back to the example of the risk prediction for the walking disability, the volume of the entire leg bone could be a good marker for the prediction. It is also possible that the loss of bone is a systemic event and the bone mass of the entire body could be even a better marker. We cannot also deny a possibility that the "leg volume", which is the combination of the leg bones and leg muscles, would be a better marker, because the amount of the muscle could also be an important factor for the prediction. Embodiments of the invention points out that anatomical entities (called "super-structure") at different granularity levels can be generated by combining smaller anatomical units and the way super-structures are generated can be guided by hierarchical tables based on anatomical knowledge. In one embodiment, the anatomical feature can be at least one of an abnormality, a disease, a condition, a diagnosis, or any combination thereof.

In one embodiment, the measuring can include measuring at least one of: a mean intensity of the image elements in the sub-regions; a sum of intensities of the image elements in the sub-regions; a highest intensity of the image elements in the sub-regions; and a lowest intensity of the image elements in the sub-regions.

In one embodiment, the method can further include providing other segmented imaging data having other structures of regions of interest of other subjects; and identifying a substantially same region of interest in the other imaging data as the region of interest of the subject by comparing one or more anatomical features, at multiple levels of granularity, in at least one of sizes, shapes and intensities of the structures of the segmented imaging data and the other structures of the other segmented imaging data based on similarities of the structures and the other structures.

In one embodiment, the identifying step can use a single feature vector including measures of intensity of the image elements in the sub-regions. The identifying step can include comparing the feature vector to one or more feature vectors of the other imaging data. In one embodiment, the identifying can include the feature vector exceeding a predetermined threshold. In another embodiment, the identifying further includes incorporating at least one non-anatomical feature in the mapping.

In on embodiment, the at least one non-anatomical feature can include at least one of diagnosis, functions or other clinical information. Previously, similarity measures or clinical correlations were based on the features of the 1 million voxels. However, 1 million voxels of information is noisy and includes too much data, so many of them are not relevant for important features. Thus, the hierarchical multi-granularity analysis turns the 1 million voxels into structures, upon which the subsequent analysis such as searching and correlation can be performed.

In one embodiment, the method can further include dynamically controlling the plurality of levels of granularity using a hierarchical relationship table.

In another embodiment, a structure of a template atlas at a level of the hierarchy can include structures of a template atlas at a lower level in the hierarchy. Further, an area of the image can be mapped to different sub-regions corresponding to different structures of different atlases.

The imaging data can be generated from at least one of magnetic resonance imaging (MRI), computed tomography (CT), positron emission tomography (PET), ultrasound, or nuclear tracer three-dimensional imaging. Further, the region of interest can include at least a portion of at least one of a brain, a heart, a liver, skin, a lung, another organ, one or more bones, or any combination thereof.

Another important point is that the lower level (high-granularity) data is difficult to connect to human perception. When humans see anatomy, they see anatomical objects from a high level point of view. For example, when a doctor sees the brain of a patient, he first sees the status of the entire brain and checks the level of the atrophy. Then s/he examines the gray and white matter in the five lobes. Quantitative analysis at this level of granularity is important to connect the low-level (high granularity) information to human's perception. At the higher level, it is more straightforward for doctors to appreciate the quantitative results and connect them to his perception. As he moves to lower levels, the doctor can gradually rely on more of the quantitative data because it becomes difficult to visually or conceptually grasp the quantitative results. The voxel-level (lowest level and highest granularity) results cannot often be visually confirmed because doctors do not see images in the voxel level. For an image-analysis product to be accepted in the market, the hierarchical multi-granularity data analysis and presentation can be important.

The following discussion of a study illustrates these advantages. In Djamanikova et al., "Tools for multiple granularity analysis of brain MRI data for individualized image analysis," Nueroimage. 2014 Nov. 1; 101:168-76, we tested our multiple-granularity analysis using eight Alzheimer's disease (AD) patients and ten patients in an age-matched control. We divided the brains into 5 granularity levels, defining 11, 17, 36, 54 and 254 structures in the brain. With this small number of patients, we did not find structures that were statistically different between the AD patients and the control subjects when the brains were divided into 36, 54, and 254 structures (high granularity analysis), but structures, such as the telencephalon, defined in the 11 and 17 labels (lower granularity analysis) could detect statistically significant volume losses in the patient group. This exemplifies how we can optimize the structural granularity levels to detect biological events of interest.

This study proposes a systematic reduction of the spatial information based on ontology-based hierarchical structural relationships. For example, 254 brain structures were first defined in multiple (n=29) geriatric atlases and five levels of ontological relationships were established, which further reduced the spatial dimension as few as 11 structures. The multiple atlases were then applied to T1-weighted MM of each subject data for automated brain parcellation. Then at each ontology level, the amount of atrophy was evaluated, providing a unique view of low-granularity analysis. This reduction of spatial information allowed us to investigate anatomical phenotypes of each patient, which were demonstrated for Alzheimer's disease and primary progressive aphasia in patients.

To analyze images from multiple subjects, identifying anatomically corresponding locations across the subjects is one of the first steps. A widely used approach is to define specific target structures, such as the hippocampus, manually, which is called the region-of-interest (ROI) approach and is considered the gold standard for the neuroanatomical research. This approach is, however, applicable to only a small portion of the anatomical structures. For example, with a 1 mm isotropic spatial resolution, a brain with a 1.2 L volume would have 1.2 million voxels. The hippocampus volume is typically about 4,000 voxels (4 ml), meaning only 0.3% of the entire voxels are evaluated. Voxel-based analysis is an alternative analysis, in which correspondence of the entire 1.2 million voxels between two brains are established automatically (see e.g. [1]). Suppose we have 50 control and 50 patient images, the entire dataset can be expressed as two matrices of $[(50\ \text{subjects})\times(1.2\ \text{million voxels})]_{Control,\ Patient}$. This voxel-vector of (1.2 million voxels) needs to be re-ordered, such that any arbitrary vector element, say, $i^{th}$ voxel of the 1.2 million-element vector, identifies the same anatomical locations across the 100 subjects. Then, we can contract the 50-element population dimension to the average and the standard deviations; the two matrices are now [(average, standard deviation)×(1.2 million voxels)]. The actual measurements can be voxel intensity (e.g., T2, fractional anisotropy, mean diffusivity) or morphometric parameters such as Jacobian, representing local atrophy or hypertrophy. This contraction can enable us to perform t-test at each voxel independently, identifying voxels with significantly different values between the two populations.

Figure 4:
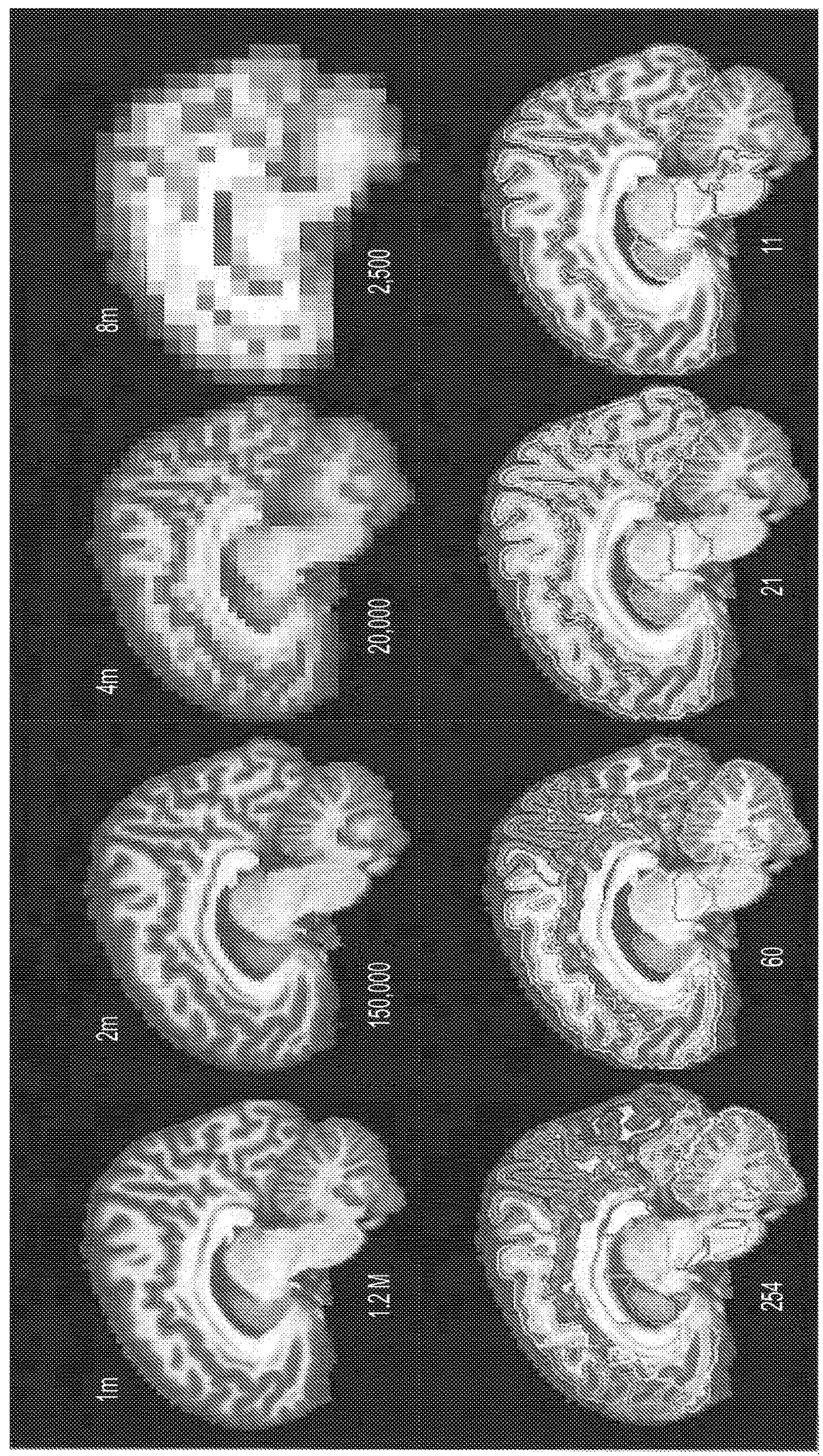
FIG. 4 depicts comparison of granularity reduction by isotropic resolution reduction (upper row) and ontology-based structural reduction (bottom row).

The voxel-based analysis is powerful because it retains the maximum amount of location information until the final statistical analysis; the entire brain is examined at the highest-possible granularity level, i.e., 1.2 million voxels. However, the limitation of this approach is also widely recognized (see e.g. [2]). First of all, the information each voxel carries is noisy. This issue is magnified by that fact that there are 1.2 million intricately dependent observations. Second, the accuracy of voxel-based registration is often in question (the 1.2 million voxel-vectors may not be well aligned across subjects). This is especially the case for two reasons; 1) lack of contrast: the voxel-to-voxel mapping between two corresponding regions is not accurate if the regions lack contrasts and 2) anatomical heterogeneity: excessive anatomical variability in certain areas, such as cortical folding, could prevent us from accurately identifying corresponding voxels between two brains in such areas. To ameliorate these issues of the high-granularity observation, it is common to reduce the level of granularity by applying a spatial filter, effectively reducing the image resolution through voxel-averaging (FIG. 4). FIG. 4 depicts comparison of granularity reduction by isotropic resolution reduction (upper row) and ontology-based structural reduction (bottom row).

In the study, we provide tools using an alternative approach to analyze the 50×1,200,000 matrices based on two concepts. First, in many clinical studies, even if the patient population is as homogenized as possible by stringent clinical criteria, a considerable amount of anatomical and, potentially pathological heterogeneity remains. After all, if the clinical information encodes enough information to purely define the patients with the same pathology, there would be less need for imaging studies; namely clinical information should be sufficient to describe the pathology. A primary interest is, therefore, to characterize the anatomical heterogeneity within a patient group. Namely, different patients may have abnormalities in different locations. If so, our interest is the first subject dimension (e.g. n=50) of the matrices and the group-aggregated statistics (reduction of the average and standard deviation) at each location is no longer an appropriate analysis. This leads us to an alternative concept, which is the reduction of the second location dimension (n=1,200,000). In VBA, this is achieved by spatial filtering. While this remains an effective approach, even with 83 reduction of the voxel size, the level of granularity remains high (2,300) while considerable amount of anatomical information is lost. For further reduction of the location dimension, anatomy-specific filtering seems a logical approach, in which a large number of voxels are grouped based on pre-defined anatomical criteria, called atlases.

This anatomy-specific filtering based on a pre-defined atlas, however, has several issues. First, the number of defined structures is limited by available image contrasts. T1-based contrast could define up to several hundred structures. If there are 300 defined structures, each structure has 4,000 voxels in average. Compared to VBA, the level of granularity is substantially low, potentially making the measurement insensitive to highly localized abnormalities. Second, there are multiple criteria to define structures and, depending on pathology, different criteria may be used. For example, for vasculature diseases, brain parcellation based on the vasculature territories may make more sense than classical ontology-based brain parcellation. Third, the accuracy issues of VBA due to the lack of the contrasts and cross-subject variability still exist for the structure-based analysis, although they may influence the results in different ways. Once the voxels are grouped to define a structure, the location information of each voxel inside the structure can degenerate and there is no longer a voxel-wise accuracy issue. Instead it may manifest as the accuracy of the boundary definition.

In this study, we developed a tool that can flexibly change the granularity level based on hierarchical relationships of 254 structures defined in our atlas. We tested this tool within a framework of a multiple-atlas brain parcellation algorithm [3-9]. Using 29 pre-parcellated atlases, test data were automatically parcellated into the smallest structural units (254 structures). Then, these structures were dynamically combined at five different hierarchical levels, down to 11 structures [10, 11]. This tool was first applied to a control group to measure test-retest reproducibility and the normal range of anatomical variability. Then we analyzed two groups of dementia populations for demonstration: Alzheimer's disease (AD) and primary progressive aphasia (PPA).

Methods:

Subjects

Three study groups were used for this study: young adult and elderly controls, AD patients, and PPA patients. All studies were approved by the Institutional Review Board of Johns Hopkins University and written informed consent was obtained.

Young adult subjects: The database for normal adult subjects was obtained from previous studies (n=17, age mean=31 years old, age range 22 to 49 years old) [12], in which each subject was scanned twice two weeks apart. Scan parameters are MPRAGE, matrix 256×256, FOV 256 mm×256 mm, slice thickness 1.2 mm, TE 3.15 ms, and TR 6.747 ms. These data were used to measure test-retest precision of the method and anatomical variability within the young normal subjects.

Alzheimer's disease (AD) patients and elderly controls: We used AD and elderly data from a study of a well-characterized group of individuals conducted by the Johns Hopkins Alzheimer's Disease Research Center (ADRC), with written informed consent in accordance with the requirements of the Johns Hopkins Institutional Review Board and the guidelines endorsed by the Alzheimer's Association [13]. Detailed demographics, health, clinical features, and initial findings were reported previously [14]. Briefly, the study sample comprised 8 patients (mean age, 75.6) who met NINCDS/ADRDA criteria for AD [15] and had a Clinical Dementia Rating (CDR) of 1 and 10 individuals (mean age, 74.3) who were cognitively normal and had a CDR=0 (normal controls or NC). The demographic characteristics of the subjects were as follows: AD—mean age=75.6 years, mean education=15.7 years, male/female=5/3 and NC—mean age=74.3, mean education=16.2 years, male/female=3/7. Subjects were excluded from enrollment if they were under the age of 55, had a history of a neurological disease other than AD, or a history of major psychiatric illness. As previously described [14], there were no differences among these groups with regard to age, sex, race, education, and the occurrence of vascular conditions, such as hypertension, hypercholesterolemia, and heart attack. Written, informed consent was obtained under the oversight of the Johns Hopkins Institutional Review Board using guidelines of the Alzheimer's Association [13]. MPRAGE scan was conducted according to the protocol of the Alzheimer's Disease Neuroimaging Initiative (ADNI) [16], with an echo time of 3.2 ms and a repetition time of 6.9 ms. The imaging matrix was 256×256, with a field of view of 240×240 mm, zero-filled to 256×256 mm and a sagittal slice thickness of 1.2 mm.

Primary progressive aphasia (PPA) subjects: n=6, mean age=70 years old, age range 56 to 84 years. Scan parameters are MPRAGE, matrix 256×256, FOV 230 mm×230 mm, slice thickness 1 mm, axial, TE 6 ms, and TR 10 ms and MPRAGE, matrix 256×256, FOV 212 mm×212 mm, 1.1 mm slice thickness, axial, TR 8.436 ms, TE 3.9 ms. The participants with PPA were seen in one of the author's (A.H.) outpatient cognitive neurology clinic at the Johns Hopkins Hospital and agreed to participate with written informed consent in accordance with the requirements of the Johns Hopkins Institutional Review Board. They were diagnosed with PPA on the basis of having a predominant and progressive deterioration in language in the absence of major change in personality, behavior or cognition other than praxis for at least two years (Mesulam, M. M. (1982). Slowly progressive aphasia without generalized dementia Annals of Neurology 11, 592-598).

Atlas Inventory:

In this study, we used multiple atlases (JHU T1 Geriatric Multi-Atlas Inventory) to perform automated brain parcellation. This atlas inventory is designed for geriatric patient populations with potential brain atrophy. The data were based on a portion of the AD/Elderly population described above; AD patients (n=15, age mean=73 years old, age range 56 to 80 years old) and normal elderly controls (n=14, age mean=75 years old, age range 60 to 80 years old). These images were parcellated into 254 structures defined in our JHU brain atlas (Eve atlas) [17-19]. This single-subject atlas was initially warped to the 29 multiple atlases using a method described by Djamanakov et al [20], followed by manual corrections for mislabels.

Image Processing

The multiple-atlas brain parcellation followed the following steps:

All T1-WIs were bias corrected and skull-stripped using SPM5 (The Wellcome Dept. of Imaging Neuroscience, London; www.fil.ion.ucl.ac.uk/spm). After initial linear alignment, all atlases were warped to the subject image using Large Deformation Diffeomorphic Metric Mapping (LDDMM) [19, 21, 22]. The transformation matrix was then applied to the co-registered parcellation maps of each atlas. The details of the multi-atlas fusion algorithm used in this study are described in our previous publication [23]. Briefly, let A be a set of atlases, with manual labels A=(I, W), where I denotes the gray-scaled T1-WI and W denotes the manual segmentations of I. Given a to-be-segmented subject with image intensity, I of the subject, at voxel i modeled as conditional Gaussian random field, conditioned on the unknown atlas and the corresponding unknown diffeomorphism. The algorithm for segmentation iterates atlas selection and diffeomorphism construction as a variant of the expectation-maximization method. Define the Q-function as the conditional expectation of the complete-data log-likelihood according to:

$$Q(W;W^{old})=E\{\log p(I,W|A)\,\text{Ç}\,I,W^{old}\}=\Sigma_i\Sigma_a P_{A_i}(a|I,W^{old})\log p(I,W|a).$$

where the sum is obtained over all voxels i and atlases a. Then the sequence of iterates W(1), W(2), . . . , is defined by the iteration:

$$W^{new}=\underset{W}{\operatorname{argmax}}\ Q(W;W^{old})$$

whose calculation is alternated with the calculations of the conditional probabilities $P_{A_i}(a|I,W^{old})$. $P_{A_i}(a|I,W^{old})$ is derived from the conditional mean of the indicator function and encodes the set of atlases being selected in the interpretation [24].

Ontology-Based Multi-Granularity Analysis Using RoiEditor:MriStudio

Figure 5A:
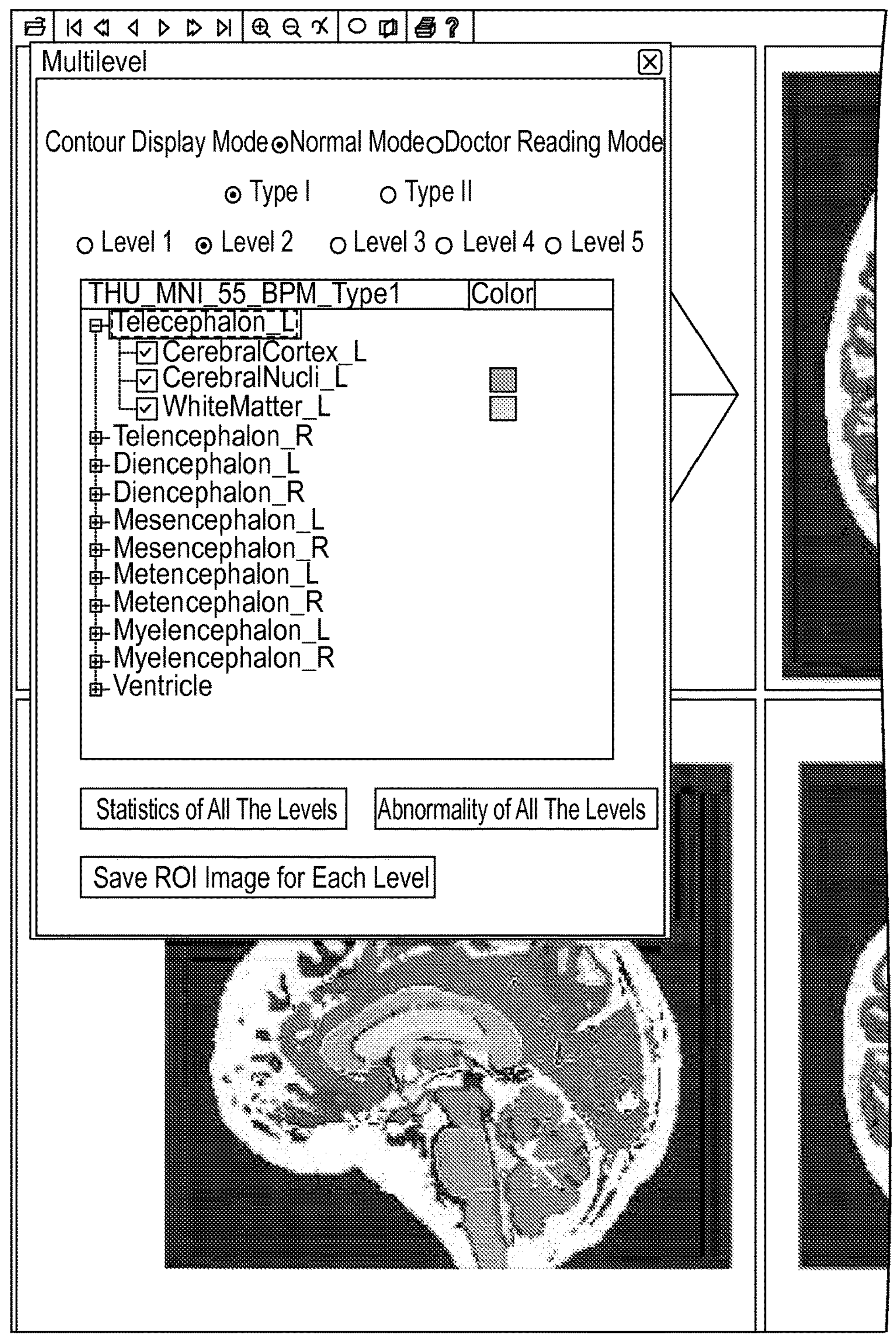
FIG. 5A depicts a screenshot of the RoiEditor interface that allows automated visualization and quantification of the ontology-based multi-granularity image analysis.
Figure 5A:
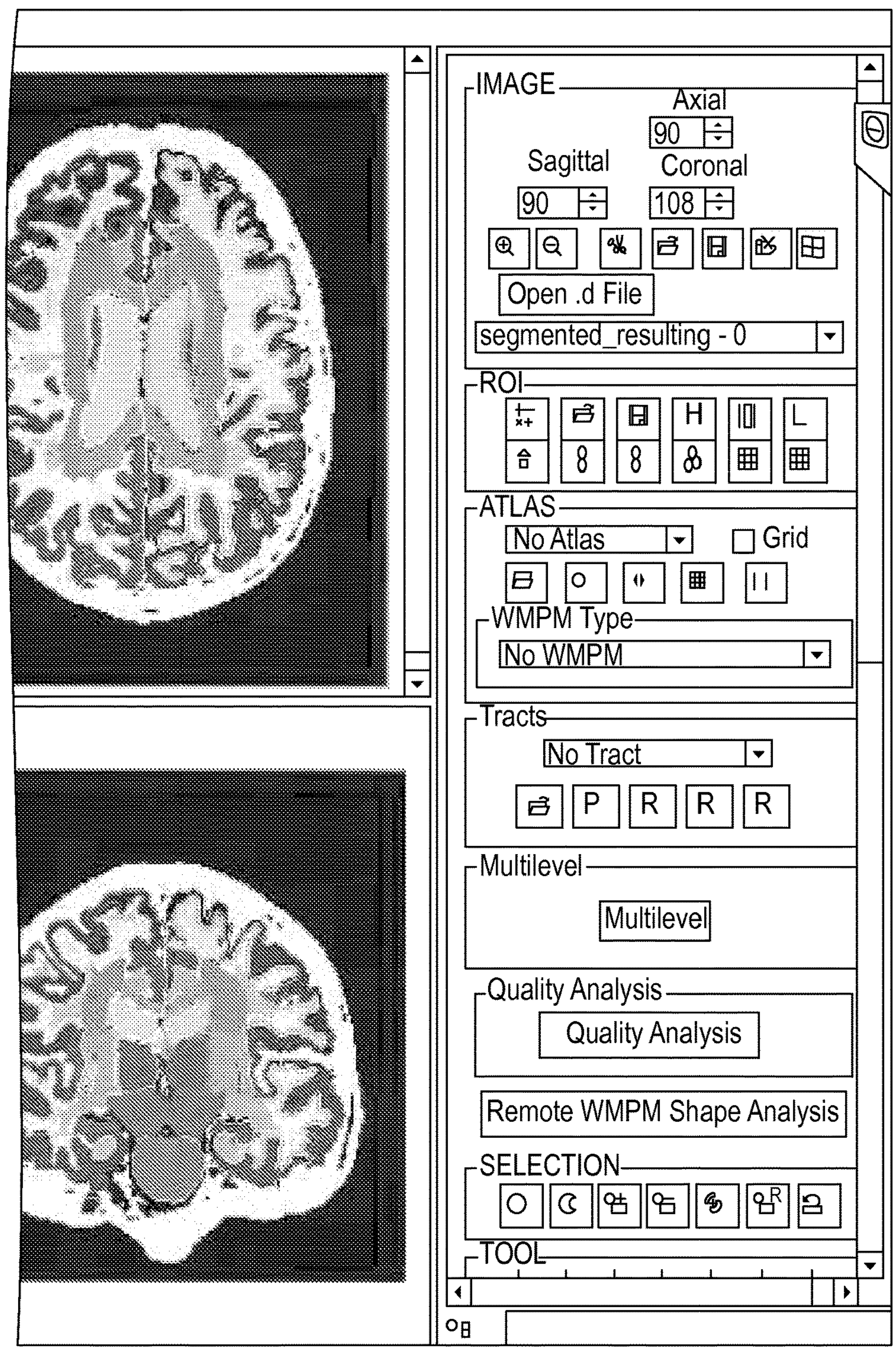

Analyses were performed using the final parcellations I the native space of the subjects. The 254 structures defined in the parcellation map were assigned a hierarchical relationship based on their ontological relationship as tabulated in Table 1. This relationship consists of five hierarchical levels. As the level goes up, the granularity of structural definition increases as; 11-17-36-54-254. This relationship is implemented in RoiEditor (X. Li, H. Jiang, and S. Mori, Johns Hopkins University, www.mristudio.org) as shown in FIGS. 4 and 5. FIG. 5 depicts a screenshot of the RoiEditor interface that allows automated visualization and quantification of the ontology-based multi-granularity image analysis. As the brain is parcellated to the multi-level structures, the sizes of all structures are calculated automatically using this software. It is important to note that only one parcellation was done for each subject, at the highest granularity level. The subsequent reparcellation to different granularity levels was achieved by the recombination of individual ROIs to create new larger ROIs as defined by the various levels of granularity. The hierarchical relationship can also be user-defined through the text file.

Test-Retest Measurements of Multi-Atlas Segmentation:

To test the test-retest reproducibility of the whole-brain multi-atlas parcellation method, the data from the twice scanned young adult subjects (n=17) were utilized. The volume data was compared for all regions of each subject across the two scans. From this dataset, the test-retest reproducibility for each subject was measured. In addition, anatomical variability among the 17 normal subjects was measured. The test-retest measurement precision and the anatomical variability were then compared using a principal component analysis.

Characterization of Anatomical Phenotypes of AD and PPA Patients:

To characterize anatomical phenotypes of AD and PPA patients, multi-atlas segmentation was performed on all patients and the multi-granularity-level analysis was performed. The anatomical feature of each patient was presented by z-scores based on the age-matched control data.

Figure 5B:
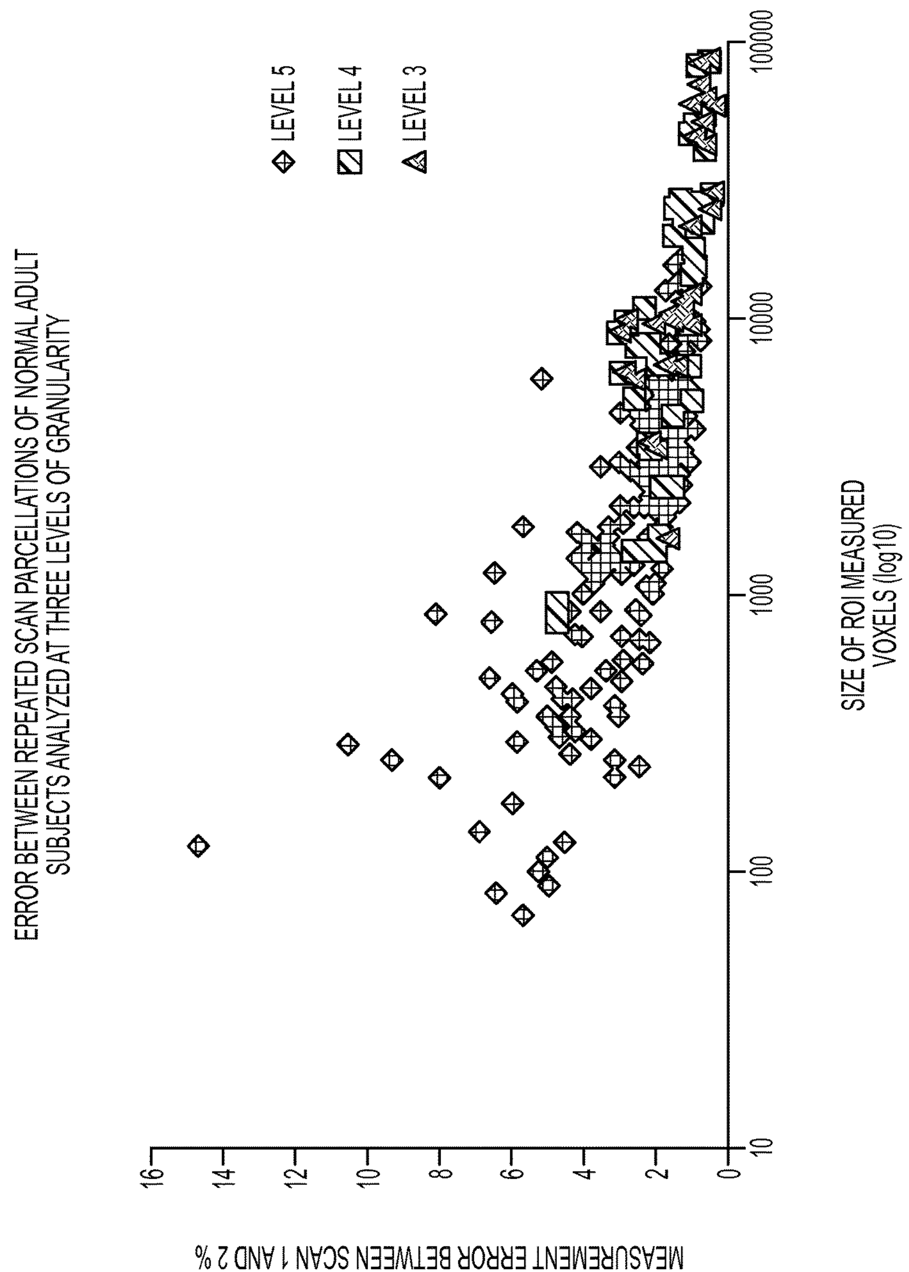
FIG. 5B depicts a test-retest analysis of healthy subjects scanned twice, according to one embodiment.

4.3 Results:

Test-Retest Reproducibility:

The test-retest variability (percent volume difference) across all ROIs between the two scans was found to be 2.6%±1.7%, 1.7%±1%, 1.4%±0.7%, 1.5%±0.7%, 1.5%±0.9% for the five different granularity levels. FIG. 5B is a plot of test-retest analysis using 17 healthy subjects, scanned twice. The variability between scans 1 and 2 is plotted as a percent of ROI size for each ROI measured at three highest granularity levels. The x-axis is the size of the structures in voxels (log 10). FIG. 5B shows the relationship between the variability and the size of the parcellation at three different granularity levels (Levels 3, 4, 5). A clear inverse relation can be seen, in which the variability increases drastically for structures less than 1000 voxels, while most of the structures larger than 1000 voxels have a small amount of variability (<2%). At Level 4, there are only two structures that are less than 1000 voxels in size and none in Levels 1-3. Consequently, the improvement in the average test-retest variability for Levels 1-4 was negligible.

Figure 6:
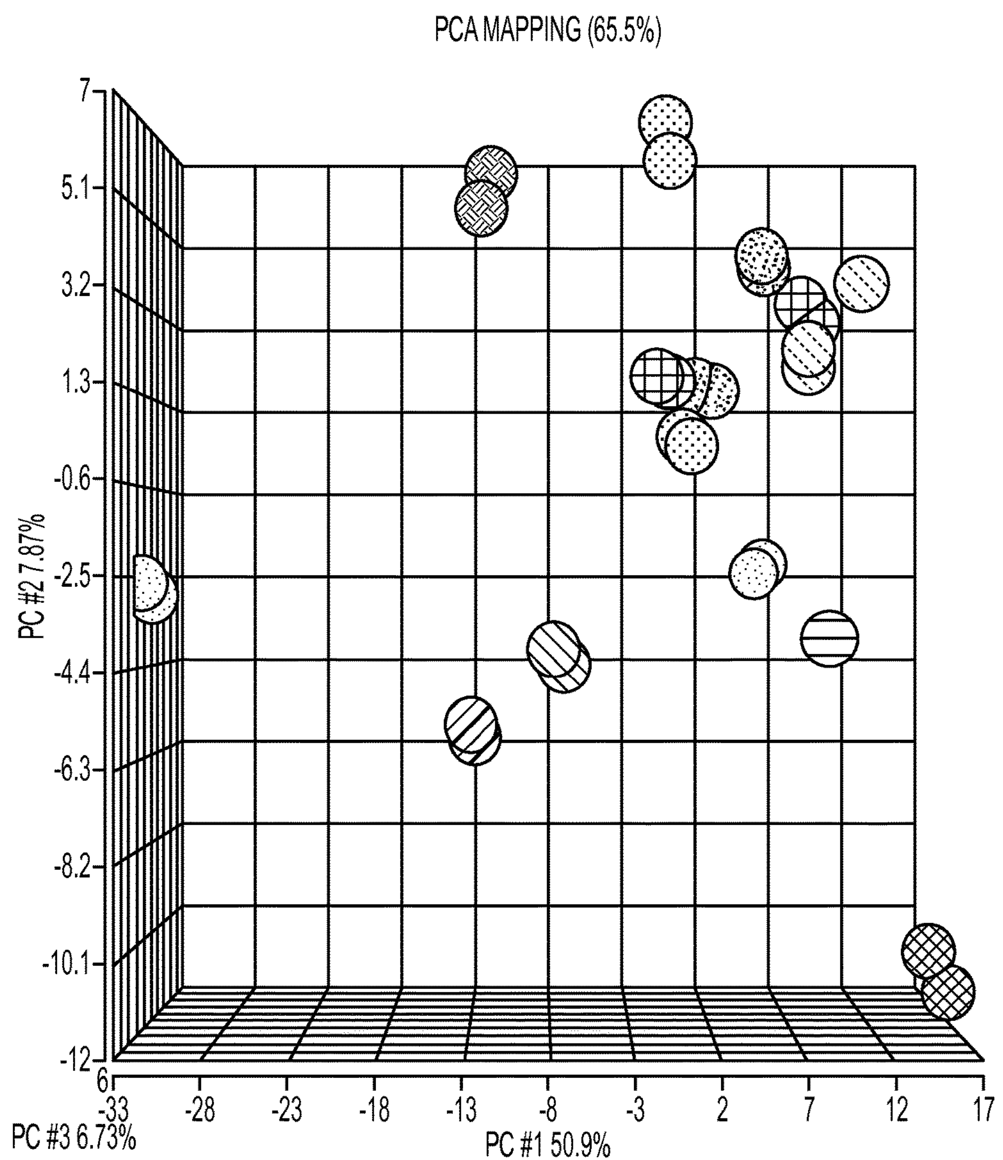
FIG. 6 shows results of principal component analysis (PCA) using the 254 ROIs in the highest granularity level.

FIG. 6 shows results of principal component analysis (PCA) using the 254 ROIs in the highest granularity level. The plot based on the first three principal components clearly isolates anatomical features of the 17 normal subjects with respect to the test-retest variability, suggesting the test-retest precision of this approach is high enough to characterize anatomical phenotypes of the normal population.

Figure 7A:
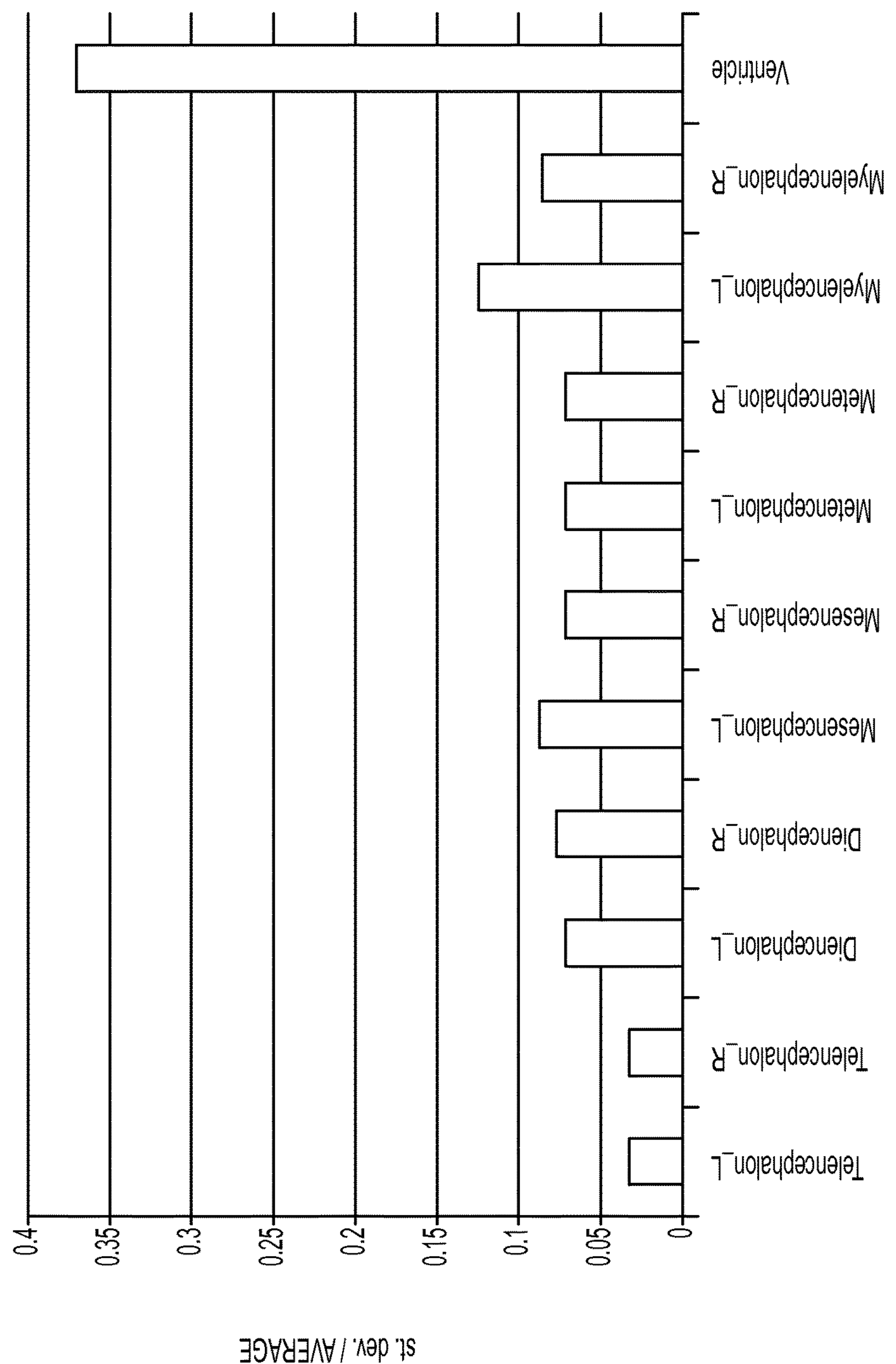
FIGS. 7A and 7B show the anatomical variability at two different granularity levels (level 1 and 4) of segmentation for the young normal adults.
Figure 7B:
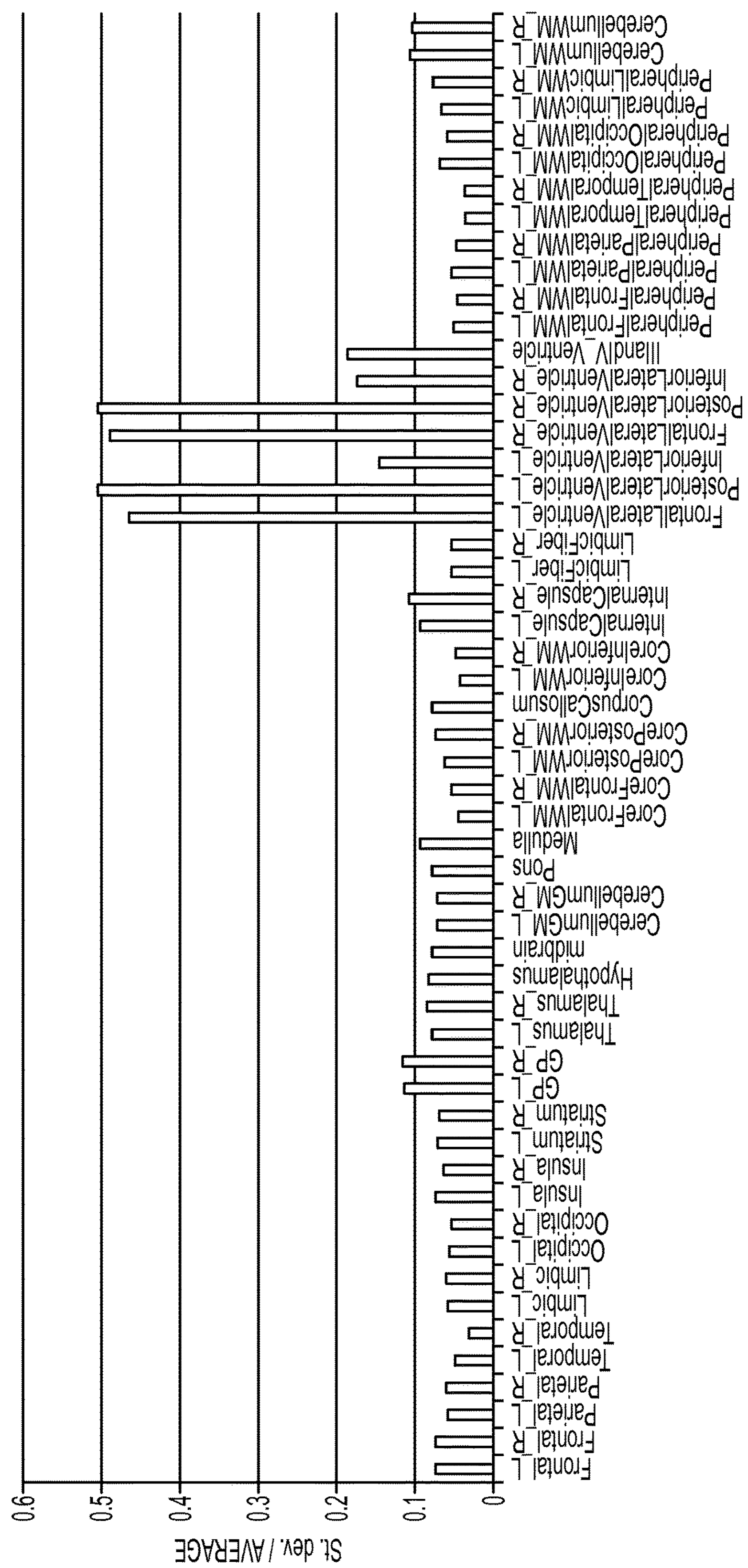

Anatomical Variation Among the Normal Subjects:

FIGS. 7A and 7B show the anatomical variability at two different granularity levels (level 1 and 4) of segmentation for the young normal adults. A few things to note are: 1) the lateral ventricles are the most variable features within normal adult populations, given that the average level of variability is at ~40% and 2) as level of granularity increases (and thus each defined structure becomes smaller), the variability tends to increase, which could be the combination of true anatomical variability and reduction of parcellation accuracy. For example, in level 1, the left telencephalon shows variability of 2.6% in the normal population. At level 2, regions that comprise the left telencephalon are the left cerebral cortex, the cortical nuclei, and the white matter (see Table 1). Their average variability was 4.0%. Further breaking down these regions into smaller subregions (i.e. the cortex is divided into the frontal, parietal, temporal, limbic, and occipital cortices) at level 3, the average variability at this level is 5.8%. This indicates the general trade-off between finer localization information and measurement precision. We can expect that the higher granularity levels, in general, provide more information about the local shape variability. For example, the Level 4 data suggest that the large population variability of the ventricle seen in Level 1 is mostly due to the large variability of the anterior and posterior lateral ventricles, while the third and fourth ventricles have much less variability.

Comparison of AD and Age-Matched Control Groups

Figure 8:
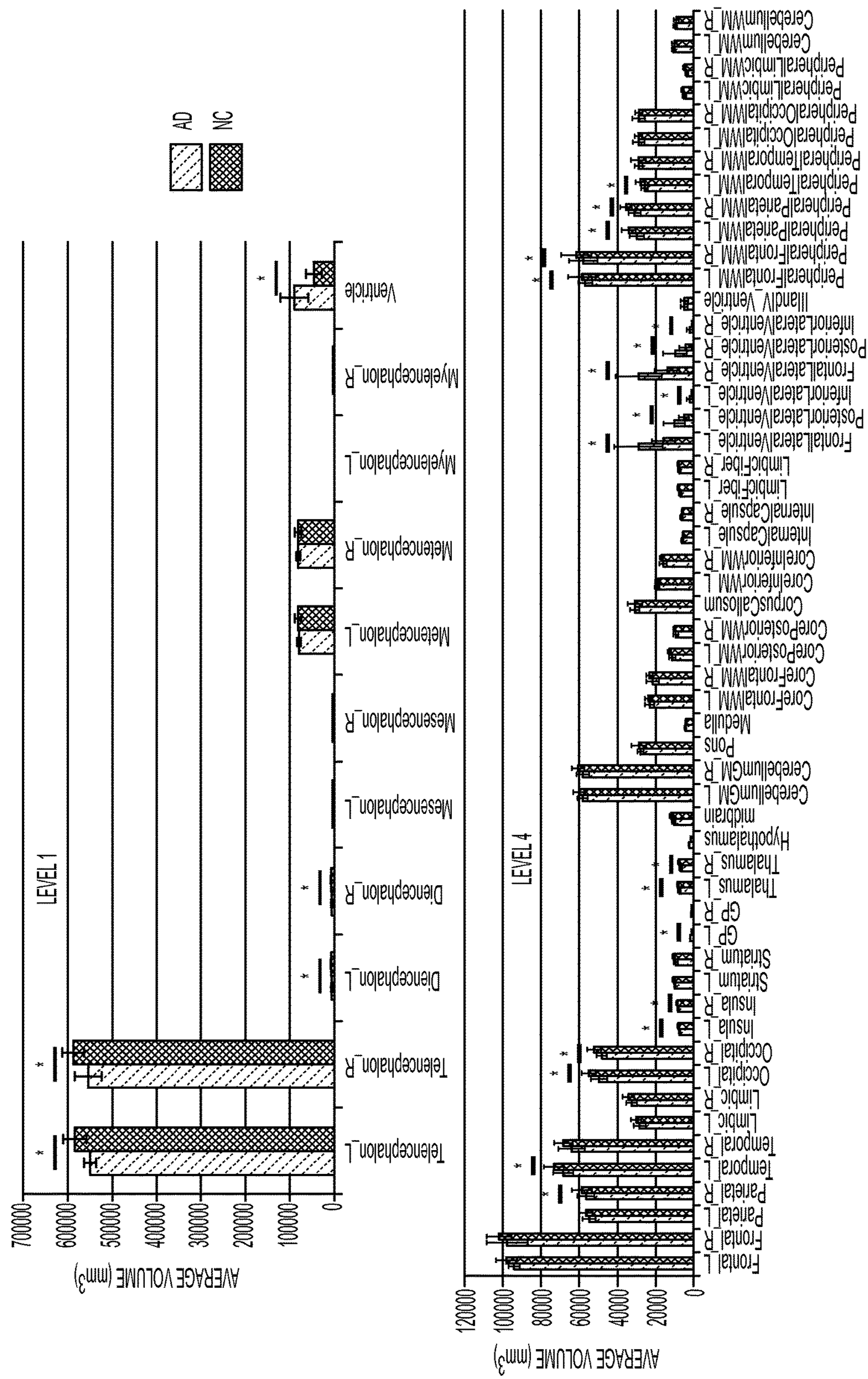
FIG. 8 shows "classical" view of anatomical abnormalities of the AD population.

FIG. 8 shows the "classical" view of anatomical abnormalities of the AD population. The graphs show that, at the lowest granularity level, a statistical difference was found at the ventricles (hypertrophy) and telencephalon and diencephalon (atrophy) between the AD and NC populations. As the granularity level increases, a more detailed view of the tissue atrophy can be obtained. At level 4, 20 structures reached statistical significance (p<0.05) between the two groups. However, after a Bonferroni multiple comparison correction, none of the regions from levels 3-5 were significantly different (p<0.05).

Individual Views of Anatomical Phenotype

Figure 9:
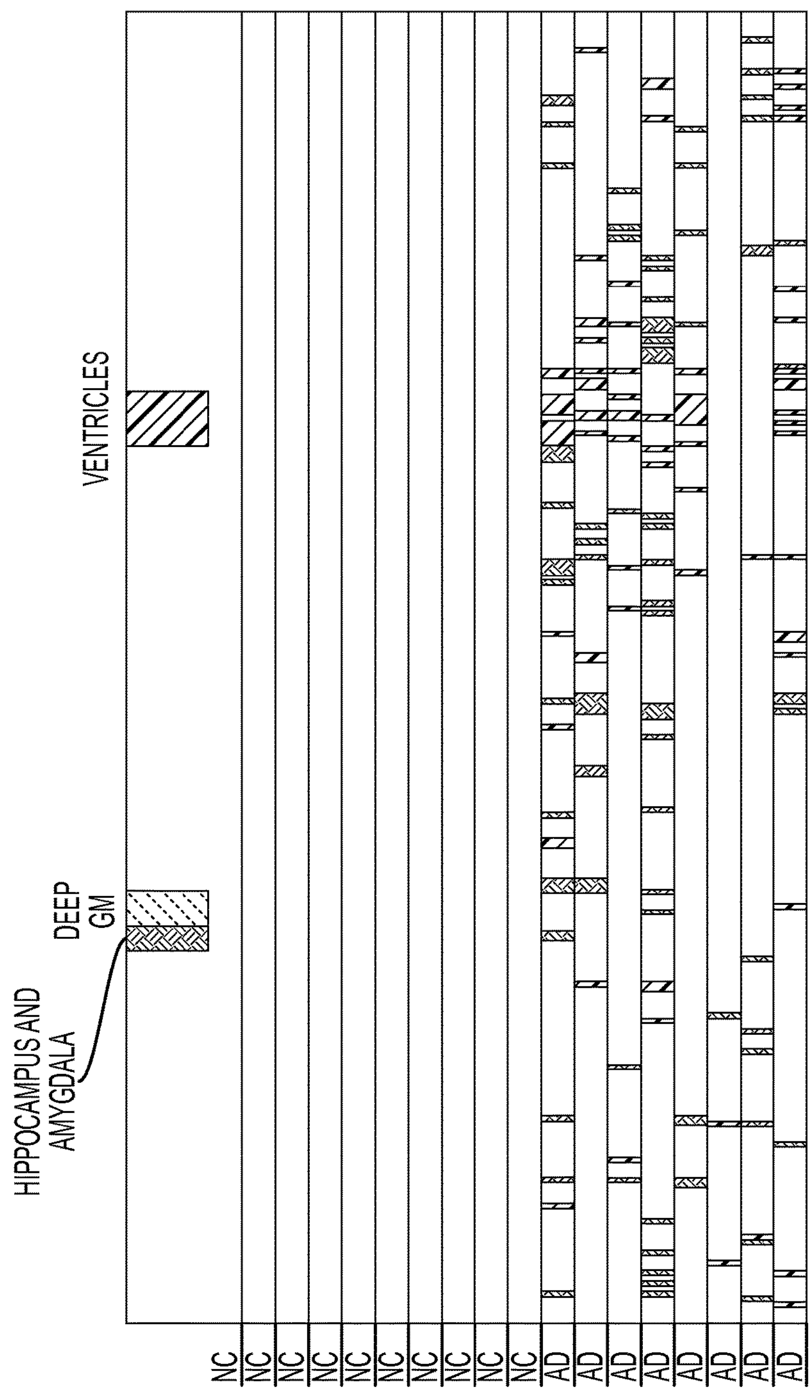
FIG. 9 shows an alternative view of the same data at level 5, in which the within-group data reduction was not performed and the anatomical phenotype of each individual is delineated using z-scores.

FIG. 9 shows an alternative view of the same data at level 5, in which the within-group data reduction was not performed and the anatomical phenotype of each individual was delineated using z-scores. In this analysis, we first calculated the average and standard deviations of the volume of each structure from the age-matched controls first and then calculate the z-score. None of the structures in the control group reached z-score higher or lower than 2. On the other hand, many "relatively" atrophic (indicated by pink) and hypertrophic (indicated by green) structures exist in the AD group. For example, the ventricles stand out as regions where many AD patients deviate substantially from the mean. However, as shown in the two example cases shown in FIG. 6, the anatomical variability within the AD population is striking. Even with this AD population with stringent inclusion criteria, the structure-by-structure population averaging could lead to: 1) loss of important patient specific anatomical features and 2) lower sensitivity due to inclusion of patients with abnormalities at different anatomical locations.

Figure 10:
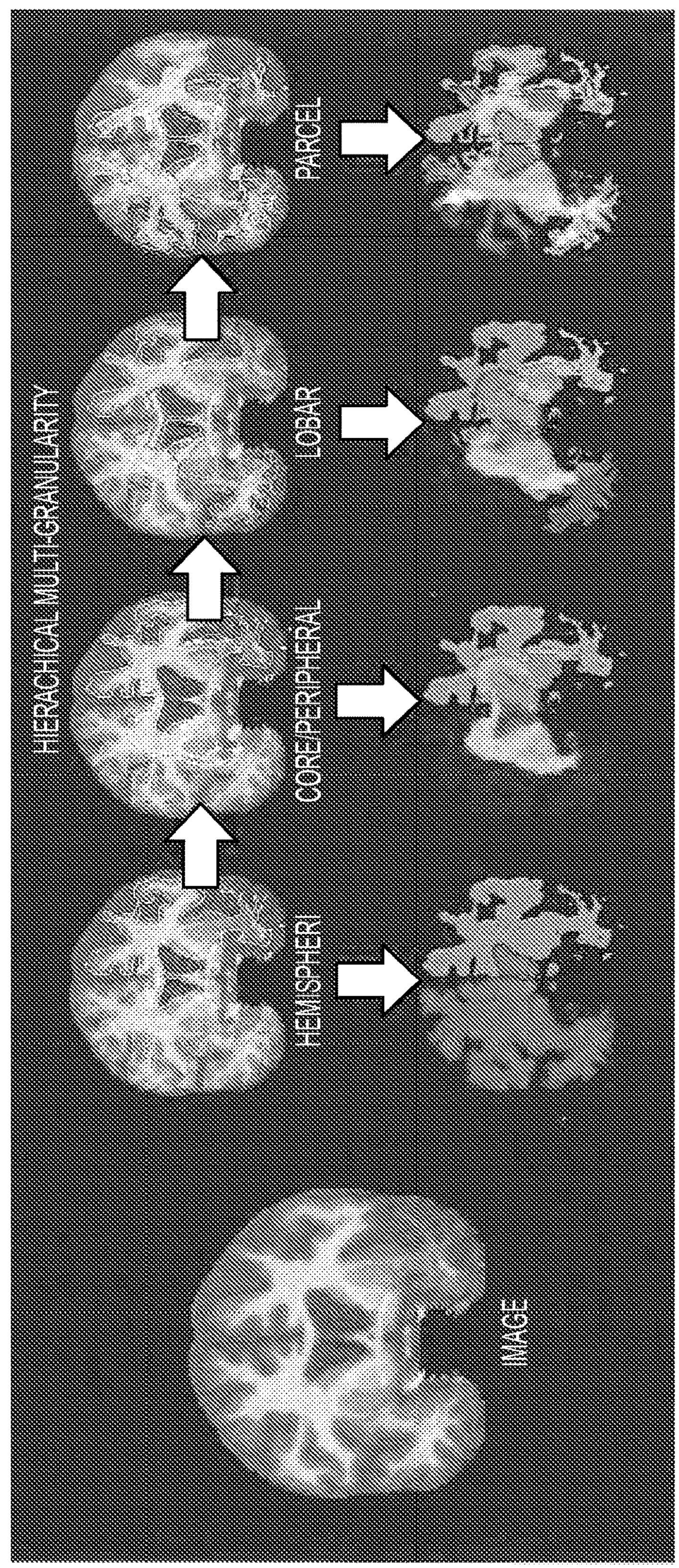
FIG. 10 shows image-based representation of the multi-granularity analysis of one PPA patients.
Figure 11:
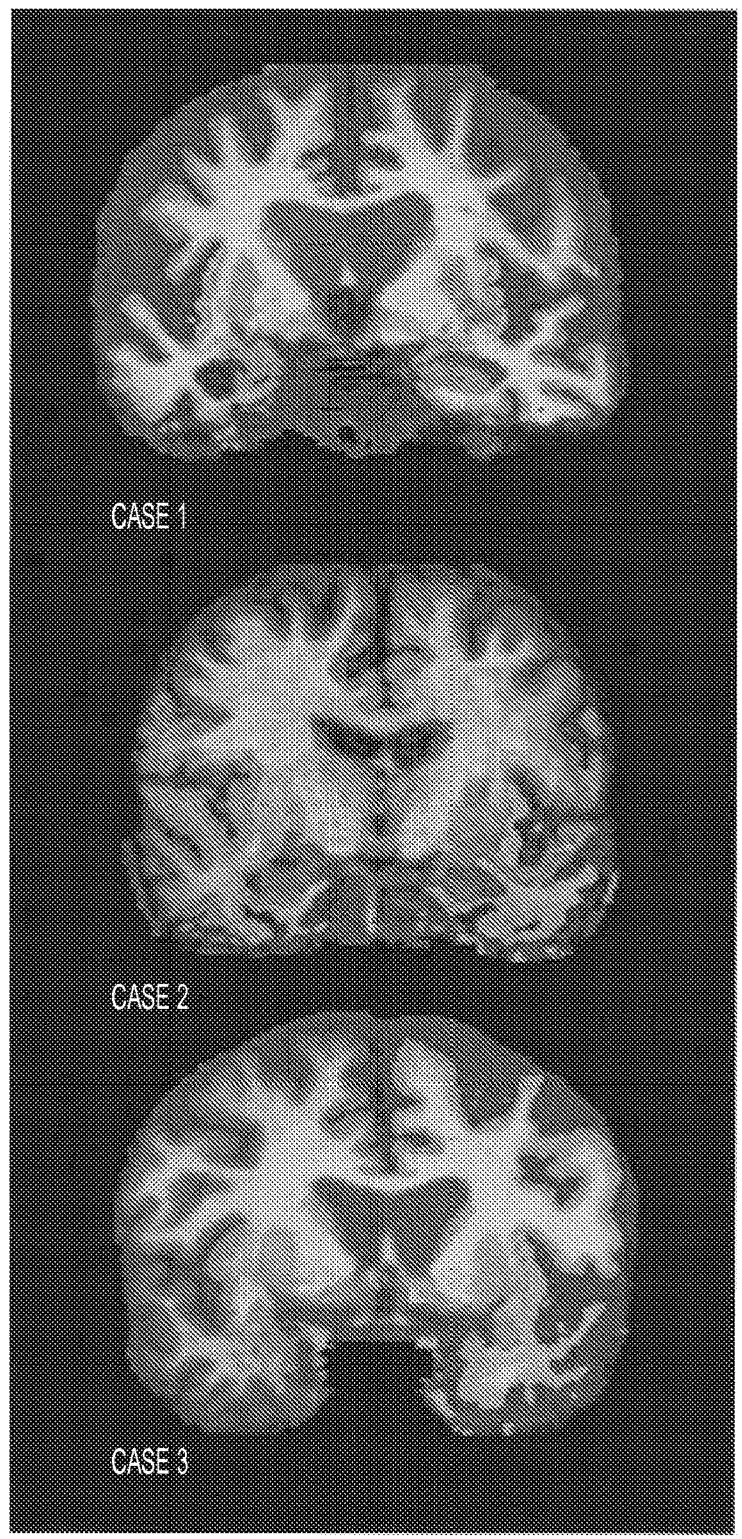
FIG. 11 shows image-based presentation of three representative PPA cases using T1-superimposition views at level 5, in which the color-coded z-score information is superimposed on their T1 weighted images.

Compared to the AD population, we expect even further within-group anatomical variability in the PPA population; these patients have been diagnosed under the umbrella term, primary progressive aphasia, based on their cognitive symptoms, specifically language memory deficits, which is known to contain various pathological mechanisms. FIG. 10 shows image-based representation of the multi-granularity analysis of one PPA patients. In this patient, the level 1 granularity analysis reveals relative size difference between the two hemisphere (the left hemisphere is smaller). As the level 2 analysis indicates lobar-level anatomical features, indicating temporal atrophy. The highest granularity level (level 5) indicates global atrophy of the left cortex and associated white matter regions, while the temporal lobe has the most severe atrophy. FIG. 11 shows image-based presentation of three representative PPA cases using T1-superimposition views at level 5, in which the color-coded z-score information is superimposed on their T1 weighted images. At a glance, we can appreciate that Patient #1 has global cortical atrophy in both hemisphere. In Patient #2, atrophy is highly focal at the left temporal lobe.

4.4 Discussion:

Tradeoff Between Granularity and Variability

The measurements of test-retest reproducibility of our automated brain parcellation by a multi-atlas approach indicated that the measurement precision was high with respect to anatomical variability among the normal subjects (FIG. 6). The test-retest precision becomes lower as the granularity increases, and at the highest granularity level, the reproducibility was 2.6+/−1.7% for all 254 measured structures. There can also be a tendency for the amount of anatomical variability among the young normal subjects to increase as the granularity increases (FIG. 7). This is probably due to the mixture of real anatomical variability and decreased level of measurement precision. In PCA (FIG. 5B), we calculate total variance of two measurements of the 17 subjects. This variance contains scanning reproducibility (test-retest), automated segmentation errors, cross-subject variability, and other sources of variability. PCA attempts to find sources of variability in the measurements and determines three most dominant sources, which, in this case, accounts for 65.9% of the total variance. The three axes are the combination of measured structures and thus do not have immediate anatomical meaning. What is important is that the two repeated measurements were naturally clustered in the PCA space with respect to the cross-subject variability. Therefore, we can conclude that reproducibility of the automated quantification method is high compared to expected amount of cross-subject variability.

The multi-granularity analysis was also applied to a well-characterized AD population and an age-matched control group. Our study sample size was small to draw a solid conclusion about anatomical abnormalities in this AD cohort but there are several findings. First, from the test-retest reproducibility and the anatomical variability among the normal population, the statistical power to detect the group difference diminishes as the granularity increases. The lower granularity analysis could detect statistical differences after multiple-comparison correction, but the findings lack detailed biological insights into the AD pathology; for example, the level 1 analysis simply tells us the AD population has brain tissue atrophy and enlarged ventricles. On the other hand, if hypothesis-driven measurements of, for example, hippocampal volumes of an AD population suggest 10% volume loss and, simultaneously, our low-granularity analysis suggests 10% volume loss of the entire gray matter, the conclusion that "hippocampal volume is different in AD population compared to the control population" may be misleading because it singles out one structure as opposed to the entire gray matter. Thus it is important to analyze not only structures of interest, but also their substructures, and greater areas to which the structures belong. From the same T1 data sets, different granularity levels offer multiple options to analyze the data with different statistical power and the different amount of anatomical specificity. From the specificity point of view, one could argue the sensitivity of analysis is at the highest when the granularity level matches the spatial extent of the abnormality; we may lose the sensitivity when the defined structures are too large (thus includes non-affected regions) or too small (divides the atrophic areas into too many regions).

Brain Parcellation Criteria

The above argument may lead to a fundamental question to all parcellation-based image analysis; "are we parcellating the brain with proper anatomical criteria?" For example, we know that the distribution of ischemic areas follow vasculature territories, but not the tissue type. If our interest is to find the affected vasculatures, the atlas we employed, which is based on tissue types, may not be appropriate. On the other hand, if we want to identify brain structures and associated functions which are affected by an infarction, a parcellation scheme that represents brain functional distribution would be needed.

The multi-granularity parcellation scheme we offer is based on the brain ontology used by the atlas by Mai et al as well as Allen Brain Institute. Here our assumption is the evolutionarily-conserved ontology-based anatomical definition is one of the most suitable ways to represent brain anatomy and functions. However, there exist multiple ontology definitions in the brain, and thus our scheme cannot be considered as the gold standard. As a matter of fact, our ontology is often not compatible with structural definitions with which we are most familiar. For example, in radiological descriptions, we often define the brain constituents as the cortex, the white matter, the deep gray nuclei, the brainstem, and the cerebellum. The brainstem is further divided into the midbrain, the pons, and the medulla. However, classical ontology divides it into the mesencephalon, metencephalon, and myelencephalon, in which the mesencephalon includes the pons and the cerebellum together. In many ataxia patients, atrophy often occurs in the pons and the cerebellum together and for a low granularity analysis, the classical ontology-based analysis could be more appropriate, but there is certainly a large degree of freedom in defining hierarchical relationship of the brain structures.

There are several important issues related to this topic. First of all, when we define ontology-based atlases, the criteria to parcellate the brain and the way we define hierarchical relationships are two different issues. The former could lead to multiple structural definitions which are mutually exclusive. For example, the same brain could be parcellated based on tissue type, classical brain structural definitions, vasculature territories, cytoarchitectures, distribution of specific receptors, etc. The latter is a question of how to combine structures defined in the highest granularity levels (in our case, 254 structures) and establish a hierarchical relationship. For the latter issue, RoiEditor provides a flexible interface to incorporate user-defined hierarchical relationships through the ontology table shown in Table 1.

The latter is also possible if users have their own brain parcellation maps. However, while the latter issue (how to combine structures and build an ontology relationship) is purely an issue of image analysis AFTER the image parcellation at the highest granularity is complete, the former issue is related to how we should parcellate the image to begin with. This issue is discussed more in detail in the next section.

One interesting question is what defines the highest granularity level: Why does our parcellation map not contain more than 254 structures? The parcellation criteria is not always exact science and arbitrary judgment is involved. However, it is generally driven by available image contrast. For example, the whole hippocampus is defined as one structure, even though we know that the hippocampus consists of many substructures. This is because we lack both resolution and contrast to sub-divide the hippocampus using conventional MRI of live human subjects. As a matter of fact, because our parcellation map was created based on T1, T2, and DTI contrasts, there are certain structures that are delineated in the atlas, but are invisible in T1-weighted images. For example, the pons area is divided into the middle cerebellar peduncle, the corticospinal tract, and the medial lemniscus, which are clearly identifiable by DTI but not in T1. Therefore, T1-weighted imaging may not have ability to detect atrophy specific to the corticospinal tract. While this level of structural granularity is relevant for DTI, they may not be reliable for T1. Therefore, the usage and interpretation of the multi-level granularity analysis requires anatomical knowledge. This issue is, however, not specific to our multi-level granularity analysis and can be applied to voxel-based analysis in general.

Multi-Atlas Approach

In this study, we employed our multi-atlas brain parcellation approach, called Diffeomorphic Probability Fusion (DPF), because we found it is generally more accurate than a single-atlas approach. However, both approaches operate under the same concept: 1) all voxels of the atlases are mapped to the corresponding voxels in a patient based on image transformation, 2) the brain structures are defined in the atlases as "parcellation map", and 3) the parcellation maps are then transferred to the patient using the transformation results from step 1). If we have only one atlas, this is a single-atlas approach. If we have multiple atlases, multiple parcellation maps are cast to a patient brain and a fusion process is required to combine the multiple maps. Our ontology-based analysis is independent to how the brain is parcellated and can be combined to the both approaches.

In the previous section, the issue of brain parcellation criteria was discussed. For example, we have four different types of the parcellation maps in our single-subject atlas called "Eve Atlas": the tissue type map used in this study, vasculature map, resting-state functional connectivity map, and cytoarchitectonic map. If a single-atlas approach is used, application of these different brain parcellation criteria is straightforward; we simply need to apply the transformation matrix to any parcellation maps of interest and warp the maps to the patient data readily. This concept can also be easily applied to the multi-atlas approach but, practically, preparing multiple atlases with multiple parcellation maps is a time consuming step that requires an extensive amount of manual work. Currently we offer 29 geriatric atlases with the 254 structural definitions. Other parcellation criteria such as the vasculature territories are not available at this moment.

Individualized Analysis

A big motivation to use the low-granularity analysis, as opposed to the voxel-based analysis is that the large reduction of spatial information from 1.2 million voxels to a mere 11-254 structures allows us to evaluate anatomical phenotypes of individual patients as shown in FIGS. 9-11. In the high-granularity analysis such as voxel-based analysis, it is common to contract the population dimension and average all patient information for each individual voxel. This approach increases the statistical power only when the entire population shares the abnormality at similar locations. This is why homogenization of pathology within a patient population through stringent inclusion criteria is vital. Our preliminary analysis of the AD population, however, revealed highly heterogeneous anatomical features (FIG. 9). The situation is far worse for the PPA population, which is known to contain multiple pathological conditions (FIGS. 10 and 11). In these situations, we cannot consider MM as a tool to conclude the pathological phenotype of the patient population as a biomarker. Like many other clinical information, it is one of the weakly discriminating factors of the patient conditions. If this is the case, the task of this ontology-based analysis is to compress the 1.2 million spatial dimension into a much smaller and standardized format, while, much like what jpeg file does to photography, losing a minimum amount of pathology information. This is an important step, if we want to combine MRI-based anatomical features with non-image clinical information such as demography, life style, clinical symptoms, lab tests, etc., to improve our ability to stratify the heterogeneous patient groups or predict the outcomes.

CONCLUSION

In this study, we introduced a new concept of low-granularity anatomical analysis based on ontology-based hierarchical relationships of the brain structures. We combined this analysis with a multi-atlas parcellation approach and applied to T1-weighted brain MM for brain atrophy analysis. Test-retest reproducibility was high. The anatomical variability of the normal population was measure at five different granularity levels, which could be used as an estimate of power calculation. This approach was then applied to AD and PPA populations. The potential of this approach to perform individual-based anatomical analysis was discussed. The proposed approach was integrated into RoiEditor for automated multi-granularity analyses.

It is important to note that the information captured at each level of the hierarchy may be represented using a single feature vector. For example, the information depicted in FIGS. 7A and 7B may be stored in the same feature vector as information about levels 2, 3, and 5. Then, the feature vector, or any other data structure capable of storing such information, may be compared with one or more other feature vectors (or any other data structure(s) capable of storing such information), to determine whether the information is similar enough. Similarity may be measured in a variety of ways, such as by meeting certain confidence intervals in statistical methods, etc.

Additionally or alternatively, the information captured at each level of the hierarchy may be represented using a single feature matrix. For example, the information depicted in FIGS. 7A and 7B may be stored in the same feature matrix as information about levels 2, 3, and 5. The matrix may be able to hold the same information as feature vectors, and may hold a series of feature vectors, e.g. those representing measurements of a subject taken over different periods of time. Thus, the matrix may be able to represent progression of anatomical characteristics over time. Just as feature vectors may be compared to find other similar feature vectors, matrices may be compared to find other similar feature matrices, e.g. patients who have similar disease progressions over time. Although these features are discussed in terms of matrices, it should be appreciated any other data structure capable of storing such information could be used, e.g. a feature vector.

A computing device may perform certain functions in response to a processor executing software instructions contained in a computer-readable medium, such as a memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device.

Numerous specific details have been set forth to provide a thorough understanding of the embodiments. It will be understood, however, that the embodiments may be practiced without these specific details. In other instances, well-known operations, components and circuits have not been described in detail so as not to obscure the embodiments. It can be appreciated that the specific structural and functional details are representative and do not necessarily limit the scope of the embodiments.

It is worthy to note that any reference to "one embodiment" or "an embodiment" means that a particular feature, structure, or characteristic described in connection with the embodiment is included in at least one embodiment. The appearances of the phrase "in one embodiment" in the specification are not necessarily all referring to the same embodiment.

Although some embodiments may be illustrated and described as comprising exemplary functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

Some embodiments may comprise an article of manufacture. An article of manufacture may comprise a computer readable storage medium to store logic. Examples of a computer readable storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible or non-transitory storage media.

It also is to be appreciated that the described embodiments illustrate exemplary implementations, and that the functional components and/or modules may be implemented in various other ways which are consistent with the described embodiments. Furthermore, the operations performed by such components or modules may be combined and/or separated for a given implementation and may be performed by a greater number or fewer number of components or modules.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated. In addition, the logic flow may be implemented by a hardware element, a software element executed by a processor, or any combination thereof.

While various exemplary embodiments have been described above, it should be understood that they have been presented by way of example only, and not limitation. Thus, the breadth and scope of the present disclosure should not be limited by any of the above-described exemplary embodiments, but should instead be defined only in accordance with the following claims and their equivalents.

REFERENCES

1. Ashburner, J. and K. J. Friston, Voxel-based morphometry—the methods. Neuroimage, 2000. 11(6 Pt 1): p. 805-21.
2. Davatzikos, C., Why voxel-based morphometric analysis should be used with great caution when characterizing group differences. Neuroimage, 2004. 23(1): p. 17-20.
3. Aljabar, P., R. A. Heckemann, A. Hammers, J. V. Hajnal, and D. Rueckert, Multi-atlas based segmentation of brain images: atlas selection and its effect on accuracy. Neuroimage, 2009. 46(3): p. 726-38.
4. Heckemann, R. A., J. V. Hajnal, P. Aljabar, D. Rueckert, and A. Hammers, Automatic anatomical brain MRI segmentation combining label propagation and decision fusion. Neuroimage, 2006. 33(1): p. 115-26.
5. Artaechevarria, X., A. Munoz-Barrutia, and C. Ortiz-de-Solorzano, Combination strategies in multi-atlas image segmentation: application to brain MR data. IEEE Trans Med Imaging, 2009. 28(8): p. 1266-77.
6. Rohlfing, T., R. Brandt, R. Menzel, and C. R. Maurer, Jr., Evaluation of atlas selection strategies for atlas-based image segmentation with application to confocal microscopy images of bee brains. Neuroimage, 2004. 21(4): p. 1428-42.
7. Langerak, T. R., U. A. van der Heide, A. N. Kotte, M. A. Viergever, M. van Vulpen, and J. P. Pluim, Label fusion in atlas-based segmentation using a selective and iterative method for performance level estimation (SIMPLE). IEEE Trans Med Imaging, 2010. 29(12): p. 2000-8.
8. Lotjonen, J. M., R. Wolz, J. R. Koikkalainen, L. Thurfjell, G. Waldemar, H. Soininen, and D. Rueckert, Fast and robust multi-atlas segmentation of brain magnetic resonance images. Neuroimage, 2010. 49(3): p. 2352-65.
9. Warfield, S. K., K. H. Zou, and W. M. Wells, Simultaneous truth and performance level estimation (STAPLE): an algorithm for the validation of image segmentation. IEEE Trans Med Imaging, 2004. 23(7): p. 903-21.
10. Mai, J., G. Paxinos, and T. Voss, Atlas of Human Brain 2007, San Diego: Academic Press.
11. Puelles, L., M. Harrison, G. Paxinos, and C. Watson, A developmental ontology for the mammalian brain based on the prosomeric model. Trends Neurosci, 2013. 36(10): p. 570-8.
12. Landman, B. A., A. J. Huang, A. Gifford, D. S. Vikram, I. A. Lim, J. A. Farrell, J. A. Bogovic, J. Hua, M. Chen, S. Jarso, S. A. Smith, S. Joel, S. Mori, J. J. Pekar, P. B. Barker, J. L. Prince, and P. C. van Zijl, Multi-parametric neuroimaging reproducibility: a 3-T resource study. Neuroimage, 2011. 54(4): p. 2854-66.
13. Research consent for cognitively impaired adults: recommendations for institutional review boards and investigators. Alzheimer Dis Assoc Disord, 2004. 18(3): p. 171-5.
14. Mielke, M. M., N. A. Kozauer, K. C. Chan, M. George, J. Toroney, M. Zerrate, K. Bandeen-Roche, M. C. Wang, P. Vanzijl, J. J. Pekar, S. Mori, C. G. Lyketsos, and M. Albert, Regionally-specific diffusion tensor imaging in mild cognitive impairment and Alzheimer's disease. Neuroimage, 2009. 46(1): p. 47-55.
15. McKhann, G., D. Drachman, M. Folstein, R. Katzman, D. Price, and E. M. Stadlan, Clinical diagnosis of Alzheimer's disease: report of the NINCDS-ADRDA Work Group under the auspices of Department of Health and Human Services Task Force on Alzheimer's Disease. Neurology, 1984. 34(7): p. 939-44.
16. Jack, C. R., Jr., M. A. Bernstein, N. C. Fox, P. Thompson, G. Alexander, D. Harvey, B. Borowski, P. J. Britson, L. W. J, C. Ward, A. M. Dale, J. P. Felmlee, J. L. Gunter, D. L. Hill, R. Killiany, N. Schuff, S. Fox-Bosetti, C. Lin, C. Studholme, C. S. DeCarli, G. Krueger, H. A. Ward, G. J. Metzger, K. T. Scott, R. Mallozzi, D. Blezek, J. Levy, J. P. Debbins, A. S. Fleisher, M. Albert, R. Green, G. Bartzokis, G. Glover, J. Mugler, and M. W. Weiner, The Alzheimer's Disease Neuroimaging Initiative (ADNI): MRI methods. J Magn Reson Imaging, 2008. 27(4): p. 685-91.
17. Faria, A. V., J. Y. Zhang, K. Oishi, X. Li, H. Y. Jiang, K. Akhter, L. Hermoye, S. K. Lee, A. Hoon, E. Stashinko, M. I. Miller, P. C. M. van Zijl, and S. Mori, Atlas-based analysis of neurodevelopment from infancy to adulthood using diffusion tensor imaging and applications for automated abnormality detection. Neuroimage, 2010. 52(2): p. 415-428.
18. Mori, S., K. Oishi, H. Jiang, L. Jiang, X. Li, K. Akhter, K. Hua, A. V. Faria, A. Mahmood, R. Woods, A. W. Toga, G. B. Pike, P. R. Neto, A. Evans, J. Zhang, H. Huang, M. I. Miller, P. van Zijl, and J. Mazziotta, Stereotaxic white matter atlas based on diffusion tensor imaging in an ICBM template. Neuroimage, 2008. 40(2): p. 570-82.
19. Oishi, K., A. Faria, H. Jiang, X. Li, K. Akhter, J. Zhang, J. T. Hsu, M. I. Miller, P. C. van Zijl, M. Albert, C. G.

Lyketsos, R. Woods, A. W. Toga, G. B. Pike, P. Rosa-Neto, A. Evans, J. Mazziotta, and S. Mori, Atlas-based whole brain white matter analysis using Large Deformation Diffeomorphic Metric Mapping: Application to normal elderly and Alzheimer's disease participants. Neuroimage, 2009.

20. Djamanakova, A., A. V. Faria, J. Hsu, C. Ceritoglu, K. Oishi, M. I. Miller, A. E. Hillis, and S. Mori, Diffeomorphic brain mapping based on T1-weighted images: Improvement of registration accuracy by multichannel mapping. Journal of Magnetic Resonance Imaging, 2013. 37(1): p. 76-84.

21. Ceritoglu, C., K. Oishi, X. Li, M. C. Chou, L. Younes, M. Albert, C. Lyketsos, P. C. van Zijl, M. I. Miller, and S. Mori, Multi-contrast large deformation diffeomorphic metric mapping for diffusion tensor imaging. Neuroimage, 2009.

22. Christensen, G. E., S. C. Joshi, and M. I. Miller, Volumetric transformation of brain anatomy. IEEE Trans Med Imaging, 1997. 16(6): p. 864-77.

23. Tang, X., K. Oishi, A. V. Faria, A. E. Hillis, M. Albert, S. Mori, and M. I. Miller, Bayesian parameter estimation and segmentation in the multi-atlas random orbit model. PLOS ONE, 2013. in press.

24. Tang, X., K. Oishi, A. V. Faria, A. E. Hillis, M. S. Albert, S. Mori, and M. I. Miller, Bayesian Parameter Estimation and Segmentation in the Multi-Atlas Random Orbit Model. PloS One, 2013. 8(6): p. e65591.

The invention claimed is:

1. A computer-implemented method of segmenting imaging data of at least one subject, comprising:

receiving imaging data comprising a plurality of image elements of the region of interest of the at least one subject;

segmenting, using at least one data processor, the imaging data of the region of interest of the at least one subject into a plurality of sub-regions corresponding to various structures at a plurality of levels of granularity, the plurality of levels of granularity having a relationship such that a level of granularity has fewer structures at a lower level of granularity;

calculating at each of the plurality of levels of granularity an abnormality factor or risk factor for the segmented various structures of said region of interest, to provide a segmented said region of interest of said subject with at least one of said abnormality factor or risk factor associated therewith;

providing at least one template atlas for said region of interest of the at least one subject;

providing other segmented imaging data having other structures of regions of interest of other subjects; and identifying a substantially same region of interest in the other imaging data as the region of interest of the at least one subject by comparing one or more anatomical features, at multiple levels of granularity, in at least one of sizes, shapes and intensities of the structures of the segmented imaging data and the other structures of the other segmented imaging data based on similarities of the structures and the other structures, to associate said abnormality factor or risk factor with said identified region of interest of said other imaging data, wherein the various structures at each level of granularity are predefined in said at least one template atlas;

wherein said segmenting includes applying said at least one template atlas to said received imaging data at each level of granularity;

wherein the segmenting includes:

measuring at least one of sizes, shapes and intensities of the various structures at each level of granularity, and performing single-subject or population-based labeling of the various structures to characterize anatomical features of the region of interest; and wherein the anatomical feature is at least one of an abnormality, a disease, a condition, a diagnosis, or any combination thereof.

2. The method of claim 1, further comprising:

co-registering said received imaging data to said at least one template atlas.

3. The method of claim 2, further comprising:

for each atlas in the at least one template atlas, filtering the imaging data to a granularity of the atlas before co-registering the imaging data to the atlas.

4. The method of claim 1, wherein the measuring includes measuring at least one of:

a mean intensity of the image elements in each sub-region;

a sum of intensities of the image elements in each sub-region;

a highest intensity of the image elements in each sub-region; and a lowest intensity of the image elements in each sub-region.

5. The method of claim 1, wherein the identifying uses a single feature vector comprising measures of intensity of the image elements in the sub-regions.

6. The method of claim 5, wherein the identifying includes comparing the feature vector to one or more feature vectors of the other imaging data.

7. The method of claim 5, wherein the identifying includes the feature vector exceeding a predetermined threshold.

8. The method of claim 1, wherein:

the at least one template atlas includes at least one of normal region of interest template data and abnormal region of interest template data, the segmenting includes applying the received imaging data to at least one of said normal region of interest template data and said abnormal region of interest template data, and the calculating is based on the received imaging data fitting within either the normal region of interest template data or the abnormal region of interest template data at a statistically significant level.

9. The method of claim 1, further comprising dynamically controlling the plurality of levels of granularity using a hierarchical relationship table.

10. The method of claim 1, wherein a structure of a template atlas at a level of the hierarchy comprises structures of a template atlas at a lower level in the hierarchy.

11. The method of claim 1, wherein an area of the imaging data is mapped to different sub-regions corresponding to different structures of different atlases.

12. The method of claim 1, wherein the image is generated from at least one of magnetic resonance imaging (MRI), computed tomography (CT), positron emission tomography (PET), ultrasound, or nuclear tracer three-dimensional imaging.

13. The method of claim 1, wherein the region of interest comprises at least a portion of at least one of a brain, a heart, a liver, skin, a lung, another organ, one or more bones, or any combination thereof.

14. The method of claim 1, wherein an image element of the plurality of image elements is placed into at least two of the sets of sub-regions.

15. The method of claim 1, wherein the plurality of image elements are pixels or voxels and wherein the relationship is hierarchical.

16. A computer-implemented method of segmenting imaging data of at least one subject, comprising:

receiving imaging data comprising a plurality of image elements of the region of interest of the at least one subject;

segmenting, using at least one data processor, the imaging data of the region of interest of the at least one subject into a plurality of sub-regions corresponding to various structures at a plurality of levels of granularity, the plurality of levels of granularity having a relationship such that a level of granularity has fewer structures at a lower level of granularity;

calculating at each of the plurality of levels of granularity an abnormality factor or risk factor for the segmented various structures of said region of interest, to provide a segmented said region of interest of said subject with at least one of said abnormality factor or risk factor associated therewith;

providing at least one template atlas for said region of interest of the at least one subject;

providing other segmented imaging data having other structures of regions of interest of other subjects; and identifying a substantially same region of interest in the other imaging data as the region of interest of the at least one subject by comparing one or more anatomical features, at multiple levels of granularity, in at least one of sizes, shapes and intensities of the structures of the segmented imaging data and the other structures of the other segmented imaging data based on similarities of the structures and the other structures, to associate said abnormality factor or risk factor with said identified region of interest of said other imaging data, wherein the various structures at each level of granularity are predefined in said at least one template atlas;

wherein said segmenting includes applying said at least one template atlas to said received imaging data at each level of granularity;

wherein the segmenting includes:

measuring at least one of sizes, shapes and intensities of the various structures at each level of granularity, and performing single-subject or population-based labeling of the various structures to characterize anatomical features of the region of interest; and wherein the identifying further includes incorporating at least one non-anatomical feature in the mapping.

17. The method of claim 16, wherein the at least one non-anatomical feature includes at least one of diagnosis, functions or other clinical information.

18. The method of claim 16, further comprising:

co-registering said received imaging data to said at least one template atlas.

19. The method of claim 16, wherein the measuring includes measuring at least one of:

a mean intensity of the image elements in each sub-region;

a sum of intensities of the image elements in each sub-region;

a highest intensity of the image elements in each sub-region; and a lowest intensity of the image elements in each sub-region.

20. The method of claim 16, wherein the identifying uses a single feature vector comprising measures of intensity of the image elements in the sub-regions.

21. A computer system for searching for one or more images having a region of interest similar to the region of a subject, the computer system comprising:

a memory storing computer-executable instructions; and at least one data processor that is coupled to the memory and that is configured to execute the computer-executable instructions to:

receive imaging data comprising a plurality of image elements of the region of interest of the at least one subject;

segment the imaging data of the region of interest of the at least one subject into a plurality of sub-regions corresponding to various structures at a plurality of levels of granularity, the plurality of levels of granularity having a relationship such that a level of granularity has fewer structures at a lower level of granularity;

calculate at each of the plurality of levels of granularity an abnormality factor or risk factor for the segmented various structures of said region of interest, to provide a segmented said region of interest of said subject with at least one of said abnormality factor or risk factor associated therewith;

provide at least one template atlas for said region of interest of the at least one subject;

provide other segmented imaging data having other structures of regions of interest of other subjects; and identify a substantially same region of interest in the other imaging data as the region of interest of the at least one subject by comparing one or more anatomical features, at multiple levels of granularity, in at least one of sizes, shapes and intensities of the structures of the segmented imaging data and the other structures of the other segmented imaging data based on similarities of the structures and the other structures, to associate said abnormality factor or risk factor with said identified region of interest of said other imaging data, wherein the various structures at each level of granularity are predefined in said at least one template atlas;

wherein said segmenting includes applying said at least one template atlas to said received imaging data at each level of granularity;

wherein the segmenting includes:

measuring at least one of sizes, shapes and intensities of the various structures at each level of granularity, and performing single-subject or population-based labeling of the various structures to characterize anatomical features of the region of interest; and wherein the anatomical feature is at least one of an abnormality, a disease, a condition, a diagnosis, or any combination thereof.

22. The computer system of claim 21, further comprising instructions that, when executed by the at least one data processor, is configured to:

co-register said received imaging data to said at least one template atlas.

23. The computer system of claim 22, further comprising instructions that, when executed by the at least one data processor, perform:

for each atlas in the at least one template atlas, filtering the imaging data to a granularity of the atlas before co-registering the imaging data to the atlas.

24. The computer system of claim 21, wherein the measuring includes measuring at least one of:

a mean intensity of the image elements in each sub-region;

a sum of intensities of the image elements in each sub-region;

a highest intensity of the image elements in each sub-region; and a lowest intensity of the image elements in each sub-region.

25. The computer system of claim 21, wherein the identifying uses a single feature vector comprising measures of intensity of the image elements in the sub-regions.

26. The computer system of claim 25, wherein the identifying includes comparing the feature vector to one or more feature vectors of the other imaging data.

27. The computer system of claim 25, wherein the identifying includes the feature vector exceeding a predetermined threshold.

28. The computer system of claim 21, wherein:

the at least one template atlas includes at least one of normal region of interest template data and abnormal region of interest template data, the segmenting includes applying the received imaging data to at least one of said normal region of interest template data and said abnormal region of interest template data, and the calculating is based on the received imaging data fitting within either the normal region of interest template data or the abnormal region of interest template data at a statistically significant level.

29. The computer system of claim 21, further comprising instructions that, when executed by the at least one data processor, is configured to dynamically control the plurality of levels of granularity using a hierarchical relationship table.

30. The computer system of claim 21, wherein a structure of a template atlas at a level of the hierarchy comprises structures of a template atlas at a lower level in the hierarchy.

31. The computer system of claim 21, wherein an area of the imaging data is mapped to different sub-regions corresponding to different structures of different atlases.

32. The computer system of claim 21, wherein the image is generated from at least one of magnetic resonance imaging (MRI), computed tomography (CT), positron emission-tomography (PET), ultrasound, or nuclear tracer three-dimensional imaging.

33. The computer system of claim 21, wherein the region of interest comprises at least a portion of at least one of a brain, a heart, a liver, skin, a lung, another organ, one or more bones, or any combination thereof.

34. The computer system of claim 21, wherein an image element of the plurality of image elements is placed into at least two of the sets of sub-regions.

35. The computer system of claim 21, wherein the plurality of image elements are pixels or voxels and wherein the relationship is hierarchical.

36. A computer system for searching for one or more images having a region of interest similar to the region of a subject, the computer system comprising:

a memory storing computer-executable instructions; and at least one data processor that is coupled to the memory and that is configured to execute the computer-executable instructions to:

receive imaging data comprising a plurality of image elements of the region of interest of the at least one subject;

segment the imaging data of the region of interest of the at least one subject into a plurality of sub-regions corresponding to various structures at a plurality of levels of granularity, the plurality of levels of granularity having a relationship such that a level of granularity has fewer structures at a lower level of granularity;

calculate at each of the plurality of levels of granularity an abnormality factor or risk factor for the segmented various structures of said region of interest, to provide a segmented said region of interest of said subject with at least one of said abnormality factor or risk factor associated therewith;

provide at least one template atlas for said region of interest of the at least one subject;

provide other segmented imaging data having other structures of regions of interest of other subjects; and identify a substantially same region of interest in the other imaging data as the region of interest of the at least one subject by comparing one or more anatomical features, at multiple levels of granularity, in at least one of sizes, shapes and intensities of the structures of the segmented imaging data and the other structures of the other segmented imaging data based on similarities of the structures and the other structures, to associate said abnormality factor or risk factor with said identified region of interest of said other imaging data, wherein the various structures at each level of granularity are predefined in said at least one template atlas;

wherein said segmenting includes applying said at least one template atlas to said received imaging data at each level of granularity;

wherein the segmenting includes:

measuring at least one of sizes, shapes and intensities of the various structures at each level of granularity, and performing single-subject or population-based labeling of the various structures to characterize anatomical features of the region of interest; and wherein the identifying further includes incorporating at least one non-anatomical feature in the mapping.

37. The computer system of claim 36, wherein the at least one non-anatomical feature includes at least one of diagnosis, functions or other clinical information.

38. The computer system of claim 36, further comprising instructions that, when executed by the at least one data processor, is configured to:

co-register said received imaging data to said at least one template atlas.

39. The computer system of claim 36, wherein the measuring includes measuring at least one of:

a mean intensity of the image elements in each sub-region;

a sum of intensities of the image elements in each sub-region;

a highest intensity of the image elements in each sub-region; and a lowest intensity of the image elements in each sub-region.

40. The computer system of claim 36, wherein the identifying uses a single feature vector comprising measures of intensity of the image elements in the sub-regions.

41. A non-transitory computer readable storage medium for segmenting imaging data of at least one subject, the computer readable storage medium comprising instructions that, when executed by at least one data processor, enable a computing system to:

receive imaging data comprising a plurality of image elements of the region of interest of the at least one subject;

segment the imaging data of the region of interest of the at least one subject into a plurality of sub-regions corresponding to various structures at a plurality of levels of granularity, the plurality of levels of granularity having a relationship such that a level of granularity has fewer structures at a lower level of granularity;

calculate at each of the plurality of levels of granularity an abnormality factor or risk factor for the segmented various structures of said region of interest, to provide a segmented said region of interest of said subject with at least one of said abnormality factor or risk factor associated therewith;

provide at least one template atlas for said region of interest of the at least one subject;

provide other segmented imaging data having other structures of regions of interest of other subjects; and identify a substantially same region of interest in the other imaging data as the region of interest of the at least one subject by comparing one or more anatomical features, at multiple levels of granularity, in at least one of sizes, shapes and intensities of the structures of the segmented imaging data and the other structures of the other segmented imaging data based on similarities of the structures and the other structures, to associate said abnormality factor or risk factor with said identified region of interest of said other imaging data, wherein the various structures at each level of granularity are predefined in said at least one template atlas;

wherein said segmenting includes applying said at least one template atlas to said received imaging data at each level of granularity;

wherein the segmenting includes:

measuring at least one of sizes, shapes and intensities of the various structures at each level of granularity, and performing single-subject or population-based labeling of the various structures to characterize anatomical features of the region of interest; and wherein the anatomical feature is at least one of an abnormality, a disease, a condition, a diagnosis, or any combination thereof.

42. The non-transitory computer readable storage medium of claim 41, further comprising instructions that, when executed by the at least one data processor, enable the computing system to: co-register said received imaging data to said at least one template atlas.

43. The non-transitory computer readable storage medium of claim 42, further comprising instructions that, when executed by the at least one data processor, enable the computing system to:

for each atlas in the at least one template atlas, filter the imaging data to a granularity of the atlas before co-registering the imaging data to the atlas.

44. The non-transitory computer readable storage medium of claim 41, wherein the measuring includes measuring at least one of:

a mean intensity of the image elements in each sub-region;

a sum of intensities of the image elements in each sub-region;

a highest intensity of the image elements in each sub-region; and a lowest intensity of the image elements in each sub-region.

45. The non-transitory computer readable storage medium of claim 41, wherein the identifying uses a single feature vector comprising measures of intensity of the image elements in the sub-regions.

46. The non-transitory computer readable storage medium of claim 45, wherein the identifying includes comparing the feature vector to one or more feature vectors of the other imaging data.

47. The non-transitory computer readable storage medium of claim 46, wherein the identifying includes the feature vector exceeding a predetermined threshold.

48. The non-transitory computer readable storage medium of claim 41, wherein:

the at least one template atlas includes at least one of normal region of interest template data and abnormal region of interest template data, the segmenting includes applying the received imaging data to at least one of said normal region of interest template data and said abnormal region of interest template data, and the calculating is based on the received imaging data fitting within either the normal region of interest template data or the abnormal region of interest template data at a statistically significant level.

49. The non-transitory computer readable storage medium of claim 41, further comprising instructions that, when executed by the at least one data processor, enable the computing system to dynamically control the plurality of levels of granularity using a hierarchical relationship table.

50. The non-transitory computer readable storage medium of claim 41, wherein a structure of a template atlas at a level of the hierarchy comprises structures of a template atlas at a lower level in the hierarchy.

51. The non-transitory computer readable storage medium of claim 41, wherein an area of the imaging data is mapped to different sub-regions corresponding to different structures of different atlases.

52. The non-transitory computer readable storage medium of claim 41, wherein the image is generated from at least one of magnetic resonance imaging (MRI), computed tomography (CT), positron emission tomography (PET), ultrasound, or nuclear tracer three-dimensional imaging.

53. The non-transitory computer readable storage medium of claim 41, wherein the region of interest comprises at least a portion of at least one of a brain, a heart, a liver, skin, a lung, another organ, one or more bones, or any combination thereof.

54. The non-transitory computer readable storage medium of claim 41, wherein an image element of the plurality of image elements is placed into at least two of the sets of sub-regions.

55. The non-transitory computer readable storage medium of claim 41, wherein the plurality of image elements are pixels or voxels and wherein the relationship is hierarchical.

56. A non-transitory computer readable storage medium for segmenting imaging data of at least one subject, the computer readable storage medium comprising instructions that, when executed by at least one data processor, enable a computing system to:

receive imaging data comprising a plurality of image elements of the region of interest of the at least one subject;

segment the imaging data of the region of interest of the at least one subject into a plurality of sub-regions corresponding to various structures at a plurality of levels of granularity, the plurality of levels of granularity having a relationship such that a level of granularity has fewer structures at a lower level of granularity;

calculate at each of the plurality of levels of granularity an abnormality factor or risk factor for the segmented various structures of said region of interest, to provide a segmented said region of interest of said subject with at least one of said abnormality factor or risk factor associated therewith;

provide at least one template atlas for said region of interest of the at least one subject;

provide other segmented imaging data having other structures of regions of interest of other subjects; and identify a substantially same region of interest in the other imaging data as the region of interest of the at least one subject by comparing one or more anatomical features, at multiple levels of granularity, in at least one of sizes, shapes and intensities of the structures of the segmented imaging data and the other structures of the other segmented imaging data based on similarities of the structures and the other structures, to associate said abnormality factor or risk factor with said identified region of interest of said other imaging data, wherein the various structures at each level of granularity are predefined in said at least one template atlas;

wherein said segmenting includes applying said at least one template atlas to said received imaging data at each level of granularity;

wherein the segmenting includes:

measuring at least one of sizes, shapes and intensities of the various structures at each level of granularity, and performing single-subject or population-based labeling of the various structures to characterize anatomical features of the region of interest; and wherein the identifying further includes incorporating at least one non-anatomical feature in the mapping.

57. The non-transitory computer readable storage medium of claim 56, wherein the at least one non-anatomical feature includes at least one of diagnosis, functions or other clinical information.

58. The non-transitory computer readable storage medium of claim 56, further comprising instructions that, when executed by the at least one data processor, enable the computing system to:

co-register said received imaging data to said at least one template atlas.

59. The non-transitory computer readable storage medium of claim 56, wherein the measuring includes measuring at least one of:

a mean intensity of the image elements in each sub-region;

a sum of intensities of the image elements in each sub-region;

a highest intensity of the image elements in each sub-region; and a lowest intensity of the image elements in each sub-region.

60. The non-transitory computer readable storage medium of claim 56, wherein the identifying uses a single feature vector comprising measures of intensity of the image elements in the sub-regions.

* * * * *

UNITED STATES PATENT AND TRADEMARK OFFICE
CERTIFICATE OF CORRECTION

PATENT NO. : 10,074,173 B2
APPLICATION NO. : 15/101820
DATED : September 11, 2018
INVENTOR(S) : Michael I. Miller and Susumu Mori It is certified that error appears in the above-identified patent and that said Letters Patent is hereby corrected as shown below:

In the Specification

Column 1, Lines 14-21, Replace the second paragraph as follows:
STATEMENT OF GOVERNMENTAL INTEREST
This invention was made with government support under EB015909 and AG020012 awarded by the National Institutes of Health. The government has certain rights in the invention.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*